(12) United States Patent
Zucherman et al.

(10) Patent No.: US 7,520,899 B2
(45) Date of Patent: Apr. 21, 2009

(54) LATERALLY INSERTABLE ARTIFICIAL VERTEBRAL DISK REPLACEMENT IMPLANT WITH CROSSBAR SPACER

(75) Inventors: James F. Zucherman, San Francisco, CA (US); Ken Y. Hsu, San Francisco, CA (US); Steven T. Mitchell, Pleasant Hill, CA (US)

(73) Assignee: Kyphon SARL (CH)

( * ) Notice: Subject to any disclaimer, the term of this patent is extended or adjusted under 35 U.S.C. 154(b) by 589 days.

(21) Appl. No.: 10/982,638

(22) Filed: Nov. 5, 2004

(65) Prior Publication Data

US 2005/0125065 A1 Jun. 9, 2005

Related U.S. Application Data

(60) Provisional application No. 60/517,973, filed on Nov. 6, 2003, provisional application No. 60/517,791, filed on Nov. 5, 2003.

(51) Int. Cl.
*A61F 2/44* (2006.01)
(52) U.S. Cl. .................................................. 623/17.14
(58) Field of Classification Search .... 623/17.11–17.16
See application file for complete search history.

(56) References Cited

U.S. PATENT DOCUMENTS

| | | | |
|---|---|---|---|
| 2,456,806 A | 12/1948 | Wolffe | |
| 2,570,735 A * | 10/1951 | Weise | 403/58 |
| 2,677,369 A | 5/1954 | Knowles | |
| 3,426,364 A | 2/1969 | Lumb | |
| 3,867,728 A | 2/1975 | Stubstad et al. | |
| 3,875,595 A | 4/1975 | Froning | |
| 4,309,777 A | 1/1982 | Patil | |
| 4,349,921 A | 9/1982 | Kuntz | |
| 4,369,769 A | 1/1983 | Edwards | |

(Continued)

FOREIGN PATENT DOCUMENTS

CA 2015507 1/1991

(Continued)

OTHER PUBLICATIONS

*Ceramic Interspinous Block (CISB) Assisted Anterior Interbody Fusion*, Haruo Tsuji, Norikazu Hirano, Yoshiharu Katoh, Hiroshi Ohsima, Hirokazu Ishihara, Hisao Matsui, and Yohihiko Hayashi, *Journal of Spinal Disorders* vol. 3. No. 1, pp. 77-86, c1990 Raven Press, Ltd., New York.

(Continued)

*Primary Examiner*—Bruce E. Snow
(74) *Attorney, Agent, or Firm*—Haynes and Boone LLP

(57) ABSTRACT

The present invention is directed to an implant that can be placed between two adjacent vertebral bodies using a lateral insertion method. The implant is characterized as having a first end plate and a second end plate which a crossbar spacer therebetween. The crossbar spacer preferably fits within a channel on the inner surfaces of the first end plate and the second end plate, whereby the crossbar spacer allows pivots, twisting and/or rotational movement of the spine. The first end plate and the second end plate include a keel extending therefrom, whereby the keel traverses longitudinally between a first lateral side and a second opposed lateral side and is substantially perpendicular to the sagittal plane of the patient's spine.

42 Claims, 8 Drawing Sheets

U.S. PATENT DOCUMENTS

| | | |
|---|---|---|
| 4,401,112 A | 8/1983 | Rezaian |
| 4,479,491 A | 10/1984 | Martin |
| 4,501,269 A | 2/1985 | Bagby |
| 4,553,273 A | 11/1985 | Wu |
| 4,554,914 A | 11/1985 | Kapp et al. |
| 4,599,084 A | 7/1986 | Nashef |
| 4,599,086 A | 7/1986 | Doty |
| 4,636,217 A | 1/1987 | Ogilvie |
| 4,657,550 A | 4/1987 | Daher |
| 4,685,447 A | 8/1987 | Iversen et al. |
| 4,696,290 A | 9/1987 | Steffee |
| 4,714,469 A | 12/1987 | Kenna |
| 4,743,256 A | 5/1988 | Brantigan |
| 4,759,766 A | 7/1988 | Büttner-Janz et al. |
| 4,759,769 A | 7/1988 | Hedman et al. |
| 4,772,287 A | 9/1988 | Ray et al. |
| 4,790,303 A | 12/1988 | Steffee |
| 4,834,757 A | 5/1989 | Brantigan |
| 4,863,477 A | 9/1989 | Monson |
| 4,874,389 A | 10/1989 | Downey |
| 4,878,915 A | 11/1989 | Brantigan |
| 4,904,260 A | 2/1990 | Ray et al. |
| 4,904,261 A | 2/1990 | Dove et al. |
| 4,911,718 A | 3/1990 | Lee et al. |
| 4,932,969 A | 6/1990 | Frey et al. |
| 4,932,975 A | 6/1990 | Main et al. |
| 4,936,848 A | 6/1990 | Bagby |
| 4,946,378 A | 8/1990 | Hirayama et al. |
| 4,961,740 A | 10/1990 | Ray et al. |
| 4,969,888 A | 11/1990 | Scholten et al. |
| 4,997,432 A | 3/1991 | Keller |
| 5,002,576 A | 3/1991 | Fuhrmann et al. |
| 5,015,247 A | 5/1991 | Michelson |
| 5,026,373 A | 6/1991 | Ray et al. |
| 5,035,716 A | 7/1991 | Downey |
| 5,047,055 A | 9/1991 | Bao et al. |
| 5,055,104 A | 10/1991 | Ray |
| 5,059,193 A | 10/1991 | Kuslich |
| 5,059,194 A | 10/1991 | Michelson |
| 5,071,437 A | 12/1991 | Steffee |
| 5,108,438 A | 4/1992 | Stone |
| 5,108,442 A | 4/1992 | Smith |
| 5,122,130 A | 6/1992 | Keller |
| 5,123,926 A | 6/1992 | Pisharodi |
| 5,167,662 A | 12/1992 | Hayes et al. |
| 5,171,280 A | 12/1992 | Baumgartner |
| 5,171,281 A | 12/1992 | Parsons et al. |
| 5,180,381 A | 1/1993 | Aust et al. |
| 5,192,326 A | 3/1993 | Bao et al. |
| 5,192,327 A | 3/1993 | Brantigan |
| 5,246,458 A | 9/1993 | Graham |
| 5,258,031 A | 11/1993 | Salib et al. |
| 5,258,043 A | 11/1993 | Stone |
| 5,263,953 A | 11/1993 | Bagby |
| 5,290,312 A | 3/1994 | Kojimoto et al. |
| 5,306,307 A | 4/1994 | Senter |
| 5,306,308 A | 4/1994 | Gross et al. |
| 5,306,309 A | 4/1994 | Wagner et al. |
| 5,313,962 A | 5/1994 | Obenchain |
| 5,314,477 A | 5/1994 | Marnay |
| 5,314,478 A | 5/1994 | Oka et al. |
| 5,320,644 A | 6/1994 | Baumgartner |
| 5,336,223 A | 8/1994 | Rogers |
| 5,350,397 A | 9/1994 | Palermo et al. |
| 5,352,225 A | 10/1994 | Yuan et al. |
| 5,354,302 A | 10/1994 | Ko |
| 5,360,430 A | 11/1994 | Lin |
| 5,366,508 A | 11/1994 | Brekke |
| 5,370,693 A | 12/1994 | Kelman et al. |
| 5,370,697 A | 12/1994 | Baumgartner |
| 5,375,823 A | 12/1994 | Navas |
| 5,383,884 A | 1/1995 | Summers |
| 5,390,683 A | 2/1995 | Pisharodi |
| 5,395,317 A | 3/1995 | Kambin |
| 5,395,372 A | 3/1995 | Holt et al. |
| 5,397,364 A | 3/1995 | Kozak et al. |
| 5,401,269 A | 3/1995 | Büttner-Janz et al. |
| 5,415,704 A | 5/1995 | Davidson |
| 5,423,816 A | 6/1995 | Lin |
| 5,423,817 A | 6/1995 | Lin |
| 5,425,772 A | 6/1995 | Brantigan |
| 5,425,773 A | 6/1995 | Boyd et al. |
| 5,425,777 A | 6/1995 | Sarkisian et al. |
| 5,431,658 A | 7/1995 | Moskovich |
| 5,439,464 A | 8/1995 | Shapiro |
| 5,443,514 A | 8/1995 | Steffee |
| 5,443,515 A | 8/1995 | Cohen et al. |
| 5,445,639 A | 8/1995 | Kuslich et al. |
| 5,454,812 A | 10/1995 | Lin |
| 5,456,722 A | 10/1995 | McLeod et al. |
| 5,458,638 A | 10/1995 | Kuslich et al. |
| 5,458,641 A | 10/1995 | Ramirez Jimenez |
| 5,458,642 A | 10/1995 | Beer et al. |
| 5,458,643 A | 10/1995 | Oka et al. |
| 5,480,401 A | 1/1996 | Navas |
| 5,480,442 A | 1/1996 | Bertagnoli |
| 5,484,437 A | 1/1996 | Michelson |
| 5,489,307 A | 2/1996 | Kuslich et al. |
| 5,489,308 A | 2/1996 | Kuslich et al. |
| 5,505,732 A | 4/1996 | Michelson |
| 5,507,816 A | 4/1996 | Bullivant |
| 5,514,180 A | 5/1996 | Heggeness et al. |
| 5,522,899 A | 6/1996 | Michelson |
| 5,527,312 A | 6/1996 | Ray |
| 5,531,793 A | 7/1996 | Kelman et al. |
| 5,534,023 A | 7/1996 | Henley |
| 5,534,028 A | 7/1996 | Bao et al. |
| 5,534,029 A | 7/1996 | Shima |
| 5,534,030 A | 7/1996 | Navarro et al. |
| 5,534,031 A | 7/1996 | Matsuzaki et al. |
| 5,540,689 A | 7/1996 | Sanders et al. |
| 5,545,229 A | 8/1996 | Parsons et al. |
| 5,549,679 A | 8/1996 | Kuslich |
| 5,554,191 A | 9/1996 | Lahille et al. |
| 5,556,431 A | 9/1996 | Büttner-Janz |
| 5,562,736 A | 10/1996 | Ray et al. |
| 5,562,738 A | 10/1996 | Boyd et al. |
| 5,571,109 A | 11/1996 | Bertagnoli |
| 5,571,189 A | 11/1996 | Kuslich |
| 5,571,190 A | 11/1996 | Ulrich et al. |
| 5,571,192 A | 11/1996 | Schönhöffer |
| 5,591,235 A | 1/1997 | Kuslich |
| 5,593,409 A | 1/1997 | Michelson |
| 5,599,279 A | 2/1997 | Slotman et al. |
| 5,601,556 A | 2/1997 | Pisharodi |
| 5,603,713 A | 2/1997 | Aust et al. .............. 606/61 |
| 5,609,634 A | 3/1997 | Voydeville |
| 5,609,635 A | 3/1997 | Michelson |
| 5,609,636 A | 3/1997 | Kohrs et al. |
| 5,620,458 A | 4/1997 | Green et al. |
| 5,645,592 A | 7/1997 | Nicolais et al. |
| 5,645,596 A | 7/1997 | Kim et al. |
| 5,645,597 A | 7/1997 | Krapiva |
| 5,645,598 A | 7/1997 | Brosnahan, III |
| 5,653,761 A | 8/1997 | Pisharodi |
| 5,653,762 A | 8/1997 | Pisharodi |
| 5,658,335 A | 8/1997 | Allen |
| 5,658,336 A | 8/1997 | Pisharodi |
| 5,658,337 A | 8/1997 | Kohrs et al. |
| 5,669,909 A | 9/1997 | Zdeblick et al. |
| 5,674,294 A | 10/1997 | Bainville et al. |
| 5,674,295 A | 10/1997 | Ray et al. |
| 5,674,296 A | 10/1997 | Bryan et al. |
| 5,676,701 A | 10/1997 | Yuan et al. |

| | | | | | | |
|---|---|---|---|---|---|---|
| 5,676,702 A | 10/1997 | Ratron | | 6,051,648 A | 4/2000 | Rhee et al. |
| 5,683,463 A | 11/1997 | Godefroy et al. | | 6,068,630 A | 5/2000 | Zucherman |
| 5,683,464 A | 11/1997 | Wagner et al. | | 6,074,390 A | 6/2000 | Zucherman et al. |
| 5,683,465 A | 11/1997 | Shinn et al. | | 6,080,155 A | 6/2000 | Michelson |
| 5,693,100 A | 12/1997 | Pisharodi | | 6,080,158 A | 6/2000 | Lin |
| 5,697,889 A | 12/1997 | Slotman et al. | | 6,080,193 A | 6/2000 | Hochshuler et al. |
| 5,697,977 A | 12/1997 | Pisharodi | | 6,086,613 A | 7/2000 | Camino et al. |
| 5,700,292 A | 12/1997 | Margulies | | 6,090,112 A | 7/2000 | Zucherman et al. |
| 5,702,449 A | 12/1997 | McKay | | 6,093,205 A | 7/2000 | McLeod et al. |
| 5,702,450 A | 12/1997 | Bisserie | | 6,096,038 A | 8/2000 | Michelson |
| 5,702,454 A | 12/1997 | Baumgartner | | 6,096,080 A | 8/2000 | Nicholson et al. |
| 5,702,455 A | 12/1997 | Saggar | | 6,099,531 A | 8/2000 | Bonutti |
| 5,716,415 A | 2/1998 | Steffee | | 6,102,950 A | 8/2000 | Vaccaro |
| 5,716,416 A | 2/1998 | Lin | | 6,110,210 A | 8/2000 | Norton et al. |
| 5,741,253 A | 4/1998 | Michelson | | 6,111,164 A | 8/2000 | Rainey et al. |
| 5,755,732 A | 5/1998 | Green et al. | | 6,113,637 A | 9/2000 | Gill et al. |
| 5,755,796 A | 5/1998 | Ibo et al. | | 6,113,638 A | 9/2000 | Williams et al. |
| 5,755,798 A | 5/1998 | Papavero et al. | | 6,113,639 A | 9/2000 | Ray et al. |
| 5,766,252 A | 6/1998 | Henry et al. | | 6,120,502 A | 9/2000 | Michelson |
| 5,772,661 A | 6/1998 | Michelson | | 6,120,503 A | 9/2000 | Michelson |
| 5,776,196 A | 7/1998 | Matsuzaki et al. | | 6,123,705 A | 9/2000 | Michelson |
| 5,776,199 A | 7/1998 | Michelson | | 6,126,689 A | 10/2000 | Brett |
| 5,782,830 A | 7/1998 | Farris | | 6,127,597 A | 10/2000 | Beyar et al. |
| 5,782,832 A | 7/1998 | Larsen et al. | | 6,129,763 A | 10/2000 | Chauvin et al. |
| 5,782,919 A | 7/1998 | Zdeblick et al. | | 6,132,430 A | 10/2000 | Wagner |
| 5,797,909 A | 8/1998 | Michelson | | 6,132,465 A | 10/2000 | Ray et al. |
| 5,800,438 A | 9/1998 | Tuke et al. | | 6,136,001 A | 10/2000 | Michelson |
| 5,800,550 A | 9/1998 | Sertich | | 6,136,031 A | 10/2000 | Middleton |
| 5,824,093 A | 10/1998 | Ray et al. | | 6,139,579 A | 10/2000 | Steffee et al. |
| 5,824,094 A | 10/1998 | Serhan et al. | | 6,146,421 A | 11/2000 | Gordon et al. |
| 5,827,328 A | 10/1998 | Buttermann | | 6,146,422 A | 11/2000 | Lawson |
| 5,836,948 A | 11/1998 | Zucherman et al. | | 6,149,650 A | 11/2000 | Michelson |
| 5,860,973 A | 1/1999 | Michelson | | 6,149,652 A | 11/2000 | Zucherman et al. |
| 5,860,977 A | 1/1999 | Zucherman et al. | | 6,149,686 A | 11/2000 | Kuslich et al. |
| 5,865,845 A | 2/1999 | Thalgott | | 6,152,926 A | 11/2000 | Zucherman et al. |
| 5,865,846 A | 2/1999 | Bryan et al. | | 6,156,038 A | 12/2000 | Zucherman et al. |
| 5,876,404 A | 3/1999 | Zucherman et al. | | 6,156,067 A | 12/2000 | Bryan et al. |
| 5,885,292 A | 3/1999 | Moskovitz et al. | | 6,159,215 A | 12/2000 | Urbahns et al. |
| 5,885,299 A | 3/1999 | Winslow et al. | | 6,162,252 A | 12/2000 | Kuras et al. |
| 5,888,222 A | 3/1999 | Coates et al. | | 6,165,218 A | 12/2000 | Husson et al. |
| 5,888,224 A | 3/1999 | Beckers et al. | | 6,176,882 B1 | 1/2001 | Biedermann et al. |
| 5,888,226 A | 3/1999 | Rogozinski | | 6,179,874 B1 | 1/2001 | Cauthen |
| 5,888,227 A | 3/1999 | Cottle ......................... 623/17 | | 6,183,471 B1 | 2/2001 | Zucherman et al. |
| 5,891,147 A | 4/1999 | Moskovitz et al. | | 6,190,387 B1 | 2/2001 | Zucherman et al. |
| 5,893,889 A | 4/1999 | Harrington | | 6,190,414 B1 | 2/2001 | Young et al. |
| 5,893,890 A | 4/1999 | Pisharodi | | 6,193,757 B1 | 2/2001 | Foley et al. |
| 5,895,426 A | 4/1999 | Scarborough et al. | | 6,206,922 B1 | 3/2001 | Zdeblick et al. |
| 5,895,427 A | 4/1999 | Kuslich et al. | | 6,210,412 B1 | 4/2001 | Michelson |
| 5,895,428 A | 4/1999 | Berry | | 6,224,595 B1 | 5/2001 | Michelson |
| 5,899,941 A | 5/1999 | Nishijima et al. | | 6,224,607 B1 | 5/2001 | Michelson ................ 606/96 |
| 5,906,616 A | 5/1999 | Pavlov et al. | | 6,224,631 B1 | 5/2001 | Kohrs |
| 5,919,235 A | 7/1999 | Husson et al. | | 6,228,118 B1 | 5/2001 | Gordon |
| 5,928,284 A | 7/1999 | Mehdizadeh | | 6,231,609 B1 | 5/2001 | Mehdizadeh |
| 5,944,754 A | 8/1999 | Vacanti | | 6,234,705 B1 | 5/2001 | Troxell |
| 5,945,115 A | 8/1999 | Dunn et al. | | 6,235,030 B1 | 5/2001 | Zucherman et al. |
| 5,961,554 A | 10/1999 | Jamson et al. | | 6,238,397 B1 | 5/2001 | Zucherman et al. |
| 5,964,807 A | 10/1999 | Gan et al. | | 6,241,769 B1 | 6/2001 | Nicholson et al. |
| 5,976,186 A | 11/1999 | Bao et al. | | 6,241,770 B1 | 6/2001 | Michelson |
| 5,980,572 A | 11/1999 | Kim et al. | | 6,241,771 B1 | 6/2001 | Gresser et al. |
| 5,984,967 A | 11/1999 | Zdeblick et al. | | 6,245,072 B1 | 6/2001 | Zdeblick et al. |
| 5,989,291 A | 11/1999 | Ralph et al. | | 6,245,108 B1 | 6/2001 | Biscup |
| 6,001,130 A | 12/1999 | Bryan et al. | | 6,258,125 B1 | 7/2001 | Paul et al. ................ 623/17.11 |
| 6,004,573 A | 12/1999 | Rathi et al. | | 6,261,296 B1 | 7/2001 | Aebi et al. |
| 6,005,162 A | 12/1999 | Constantz | | 6,264,655 B1 | 7/2001 | Pisharodi |
| 6,019,792 A | 2/2000 | Cauthen | | 6,264,656 B1 | 7/2001 | Michelson |
| 6,019,793 A | 2/2000 | Perren et al. | | 6,264,695 B1 | 7/2001 | Stoy |
| 6,022,376 A | 2/2000 | Assell et al. | | 6,270,498 B1 | 8/2001 | Michelson |
| 6,039,761 A | 3/2000 | Li et al. | | 6,277,149 B1 | 8/2001 | Boyle et al. |
| 6,039,763 A | 3/2000 | Shelokov | | 6,280,444 B1 | 8/2001 | Zucherman et al. |
| 6,042,582 A | 3/2000 | Ray | | 6,280,475 B1 | 8/2001 | Bao et al. |
| 6,045,579 A | 4/2000 | Hochshuler et al. | | 6,287,343 B1 | 9/2001 | Kuslich et al. |
| 6,045,580 A | 4/2000 | Scarborough et al. | | 6,296,664 B1 | 10/2001 | Middleton |
| 6,048,342 A | 4/2000 | Zucherman | | 6,296,665 B1 | 10/2001 | Strnad et al. |

| | | |
|---|---|---|
| 6,302,914 B1 | 10/2001 | Michelson |
| 6,309,421 B1 | 10/2001 | Pisharodi |
| 6,311,562 B1 | 11/2001 | Hanada |
| 6,315,795 B1 | 11/2001 | Scarborough et al. |
| 6,315,797 B1 | 11/2001 | Middleton |
| 6,325,827 B1 | 12/2001 | Lin |
| 6,332,882 B1 | 12/2001 | Zucherman et al. |
| 6,332,883 B1 | 12/2001 | Zucherman et al. |
| 6,342,074 B1 | 1/2002 | Simpson |
| 6,348,071 B1 | 2/2002 | Steffee et al. |
| 6,350,283 B1 | 2/2002 | Michelson |
| 6,364,880 B1 | 4/2002 | Michelson |
| 6,368,350 B1 | 4/2002 | Erickson et al. |
| 6,368,351 B1 | 4/2002 | Glenn et al. |
| 6,371,984 B1 | 4/2002 | Van Dyke et al. |
| 6,371,988 B1 | 4/2002 | Pafford et al. |
| 6,371,989 B1 | 4/2002 | Chauvin et al. |
| 6,379,355 B1 | 4/2002 | Zucherman et al. |
| 6,379,385 B1 | 4/2002 | Kalas et al. |
| 6,383,221 B1 | 5/2002 | Scarborough et al. |
| 6,391,030 B1 | 5/2002 | Wagner et al. |
| 6,391,058 B1 | 5/2002 | Kuslich et al. |
| 6,395,030 B1 | 5/2002 | Songer et al. |
| 6,395,031 B1 | 5/2002 | Foley et al. |
| 6,395,032 B1 | 5/2002 | Gauchet |
| 6,395,034 B1 | 5/2002 | Suddaby |
| 6,402,785 B1 | 6/2002 | Zdeblick et al. |
| 6,409,766 B1 | 6/2002 | Brett |
| 6,413,278 B1 | 7/2002 | Marchosky |
| 6,416,551 B1 | 7/2002 | Keller |
| 6,419,676 B1 | 7/2002 | Zucherman et al. |
| 6,419,677 B2 | 7/2002 | Zucherman et al. |
| 6,419,704 B1 | 7/2002 | Ferree |
| 6,419,706 B1 | 7/2002 | Graf |
| 6,423,063 B1 | 7/2002 | Bonutti |
| 6,423,095 B1 | 7/2002 | Van Hoech et al. |
| 6,425,920 B1 | 7/2002 | Hamada |
| 6,432,106 B1 | 8/2002 | Fraser |
| 6,436,098 B1 | 8/2002 | Michelson |
| 6,436,119 B1 | 8/2002 | Erb et al. |
| 6,436,140 B1 | 8/2002 | Liu et al. |
| 6,436,142 B1 | 8/2002 | Paes et al. |
| 6,440,168 B1 | 8/2002 | Cauthen |
| 6,443,990 B1 | 9/2002 | Aebi et al. |
| 6,447,512 B1 | 9/2002 | Landry et al. |
| 6,447,544 B1 | 9/2002 | Michelson |
| 6,447,547 B1 | 9/2002 | Michelson |
| 6,451,019 B1 | 9/2002 | Zucherman et al. |
| 6,451,020 B1 | 9/2002 | Zucherman et al. |
| 6,454,804 B1 | 9/2002 | Ferree |
| 6,454,807 B1 | 9/2002 | Jackson |
| 6,458,131 B1 | 10/2002 | Ray |
| 6,458,159 B1 | 10/2002 | Thalgott |
| 6,461,359 B1 | 10/2002 | Tribus et al. |
| 6,468,310 B1 | 10/2002 | Ralph et al. |
| 6,471,724 B2 | 10/2002 | Zdeblick et al. |
| 6,475,219 B1 | 11/2002 | Shelokov |
| 6,478,796 B2 | 11/2002 | Zucherman et al. |
| 6,478,822 B1 | 11/2002 | Leroux et al. |
| 6,478,823 B1 | 11/2002 | Michelson |
| 6,482,233 B1 | 11/2002 | Aebi et al. |
| 6,482,235 B1 | 11/2002 | Lambrecht et al. |
| 6,485,517 B1 | 11/2002 | Michelson |
| 6,488,710 B2 | 12/2002 | Besselink |
| 6,500,178 B2 | 12/2002 | Zucherman et al. |
| 6,500,205 B1 | 12/2002 | Michelson |
| 6,503,279 B1 | 1/2003 | Webb et al. |
| 6,514,256 B2 | 2/2003 | Zucherman et al. |
| 6,517,580 B1 | 2/2003 | Ramadan et al. |
| 6,520,993 B2 | 2/2003 | James et al. |
| 6,520,996 B1 | 2/2003 | Manasas et al. |
| 6,524,312 B2 | 2/2003 | Landry et al. |
| 6,527,773 B1 | 3/2003 | Lin et al. |
| 6,527,804 B1 | 3/2003 | Gauchet et al. |
| 6,527,806 B2 | 3/2003 | Ralph et al. |
| 6,530,933 B1 | 3/2003 | Yeung et al. |
| 6,530,955 B2 | 3/2003 | Boyle et al. |
| 6,540,785 B1 | 4/2003 | Gill et al. |
| 6,547,823 B2 | 4/2003 | Scarborough et al. |
| 6,548,002 B2 | 4/2003 | Gresser et al. |
| 6,554,863 B2 | 4/2003 | Paul et al. |
| 6,558,386 B1 | 5/2003 | Cragg |
| 6,558,387 B2 | 5/2003 | Errico et al. |
| 6,558,390 B2 | 5/2003 | Cragg |
| 6,558,423 B1 | 5/2003 | Michelson |
| 6,558,424 B2 | 5/2003 | Thalgott |
| 6,562,073 B2 | 5/2003 | Foley |
| 6,562,074 B2 | 5/2003 | Gerbec et al. |
| 6,565,570 B2 | 5/2003 | Sterett et al. |
| 6,569,201 B2 | 5/2003 | Moumene et al. |
| 6,572,653 B1 | 6/2003 | Simonson |
| 6,572,654 B1 | 6/2003 | Santilli |
| 6,575,982 B1 | 6/2003 | Bonutti |
| 6,576,016 B1 | 6/2003 | Hochshuler et al. |
| 6,576,017 B2 | 6/2003 | Foley et al. |
| 6,579,318 B2 | 6/2003 | Varga et al. |
| 6,579,320 B1 | 6/2003 | Gauchet et al. |
| 6,579,321 B1 | 6/2003 | Gordon et al. |
| 6,582,432 B1 | 6/2003 | Michelson |
| 6,582,437 B2 | 6/2003 | Dorchak et al. |
| 6,582,468 B1 | 6/2003 | Gauchet |
| 6,682,562 B2 | 1/2004 | Viart et al. |
| 6,706,068 B2 | 3/2004 | Ferree ........ 623/17.11 |
| 6,706,070 B1 | 3/2004 | Wagner et al. |
| 6,740,118 B2 | 5/2004 | Eisermann et al. |
| 6,755,841 B2 | 6/2004 | Fraser et al. |
| 6,770,095 B2 | 8/2004 | Grinberg |
| 2001/0012938 A1 | 8/2001 | Zucherman |
| 2002/0128715 A1 | 9/2002 | Bryan et al. |
| 2003/0208273 A1 | 11/2003 | Eisermann et al. |
| 2004/0073313 A1 | 4/2004 | Link et al. |
| 2004/0106998 A1* | 6/2004 | Ferree ........ 623/17.16 |
| 2004/0117022 A1 | 6/2004 | Marnay et al. |
| 2004/0138750 A1 | 7/2004 | Mitchell |
| 2004/0143332 A1 | 7/2004 | Krueger |
| 2004/0225360 A1 | 11/2004 | Malone |
| 2004/0225365 A1 | 11/2004 | Eisermann et al. |
| 2004/0225366 A1 | 11/2004 | Eisermann et al. |
| 2005/0043802 A1* | 2/2005 | Eisermann et al. ........ 623/17.16 |
| 2005/0159818 A1* | 7/2005 | Blain ........ 623/17.15 |

FOREIGN PATENT DOCUMENTS

| | | |
|---|---|---|
| DE | 4012622 | 7/1991 |
| EP | 0307241 B1 | 3/1989 |
| FR | 2707864 | 1/1995 |
| FR | 2717066 | 9/1995 |
| FR | 2717068 | 9/1995 |
| FR | 2730156 A1 | 8/1996 |
| FR | 2780269 A1 | 12/1999 |
| FR | 2806614 A1 | 9/2001 |
| WO | WO 90/00037 | 1/1990 |
| WO | WO 95/31158 A | 11/1995 |
| WO | WO 99/26562 | 6/1999 |
| WO | WO 99/59669 | 11/1999 |
| WO | WO 00/04851 | 2/2000 |
| WO | WO 00/13619 | 3/2000 |
| WO | WO 00/13620 | 3/2000 |
| WO | WO 00/23015 A1 | 4/2000 |
| WO | WO 01/01893 A1 | 1/2001 |

| | | | |
|---|---|---|---|
| WO | WO 01/89428 A2 | 11/2001 | |

OTHER PUBLICATIONS

*Instrumentation and Implants for Spinal Surgery*, J. Dabb, *Diary of the XVIIIth Scientific Meeting of the PTO Tr/Pamietnik XVIII Zjazdu Naukowego PTO Tr/PZ,WL, Warszawa*, Link America Inc., 1971, 665.

*Spinal Stenosis and Neurogenic Claudication*, Richard W. Porter, MD, FRCS, FRCSE, *Spine* vol. 21, No. 17, pp. 2046-2052, c1996, Lippincott-Raven Publishers.

*Preliminary Design and Experimental Studies of a Novel Soft Implant for Correcting Sagittal Plan Instability in the Lumbar Spine*, R.J.Minns, BEng, Msc, PhD, DscTech, and W.K.Walsh, FRCS, *Spine* vol. 22, No. 16, pp. 1819-1827, c1997, Lippincott-Raven Publishers.

* cited by examiner
LATERALLY INSERTABLE ARTIFICIAL VERTEBRAL DISK REPLACEMENT IMPLANT WITH CROSSBAR SPACER

CLAIM OF PRIORITY

This application claims priority under 35 USC 119 to U.S. Patent Applications No. 60/517,791, filed Nov. 5, 2003 and entitled "ARTIFICIAL VERTEBRAL DISK REPLACEMENT IMPLANT WITH CROSSBAR SPACER AND LATERAL IMPLANT METHOD," and U.S. No. 60/517,973, filed Nov. 6, 2003 and entitled "ARTIFICIAL VERTEBRAL DISK REPLACEMENT IMPLANT WITH CROSSBAR SPACER AND LATERAL IMPLANT METHOD," both of which are hereby incorporated by reference.

CROSS-REFERENCE TO RELATED APPLICATIONS

This application is related to U.S. Provisional Application No. 60/422,039, filed Oct. 29, 2002, entitled "ARTIFICIAL VERTEBRAL DISK REPLACEMENT IMPLANT WITH TRANSLATING PIVOT POINT AND METHOD," U.S. patent application Ser. No. 10/684,668, filed Oct. 14, 2003, entitled "ARTIFICIAL VERTEBRAL DISK REPLACEMENT IMPLANT WITH CROSSBAR SPACER AND METHOD," U.S. patent application Ser. No. 10/684,669, filed Oct. 14, 2003, entitled "ARTIFICIAL VERTEBRAL DISK REPLACEMENT IMPLANT WITH TRANSLATING PIVOT POINT AND METHOD," U.S. Provisional Application No. 60/422,011, filed Oct. 29, 2002, entitled "TOOLS FOR IMPLANTING AN ARTIFICIAL VERTEBRAL DISK AND METHOD," U.S. patent application Ser. No. 10/685,134, filed Oct. 14, 2003, entitled "TOOLS FOR IMPLANTING AN ARTIFICIAL VERTEBRAL DISK AND METHOD," U.S. Provisional Application No. 60/422,022, filed Oct. 29, 2002, entitled "ARTIFICIAL VERTEBRAL DISK REPLACEMENT IMPLANT WITH A SPACER AND METHOD," U.S. Provisional Application No. 60/422,021, filed Oct. 29, 2002, entitled "ARTIFICIAL VERTEBRAL DISK REPLACEMENT IMPLANT WITH CROSSBAR SPACER AND METHOD," U.S. patent application Ser. No. 10/685,011, filed Oct. 14, 2003, entitled "ARTIFICIAL VERTEBRAL DISK REPLACEMENT IMPLANT WITH SPACER AND METHOD," U.S. patent application Ser. No. 10/981,863, filed Nov. 5, 2004 entitled "LATERALLY INSERTABLE ARTIFICIAL VERTEBRAL DISK REPLACEMENT IMPLANT WITH TRANSLATING PIVOT POINT," U.S. patent application Ser. No. 10/981,807, filed Nov. 5, 2004, entitled "METHOD OF LATERALLY INSERTING AN ARTIFICIAL VERTEBRAL DISK REPLACEMENT IMPLANT WITH TRANSLATING PIVOT POINT," U.S. patent application Ser. No. 10/981,952, filed Nov. 5, 2004, entitled "METHOD OF LATERALLY INSERTING ARTIFICIAL VERTEBRAL DISK REPLACEMENT IMPLANT WITH A CROSSBAR SPACER," U.S. patent application Ser. No. 10/981,923, filed Nov. 5, 2004, entitled "LATERALLY INSERTABLE ARTIFICIAL VERTEBRAL DISK REPLACEMENT IMPLANT WITH CURVED SPACER," U.S. patent application Ser. No. 10/981,945, filed Nov. 5, 2004, entitled "METHOD OF LATERALLY INSERTING AN ARTIFICIAL VERTEBRAL DISK REPLACEMENT IMPLANT WITH CURVED SPACER," all of which are incorporated herein by reference.

FIELD OF THE INVENTION

The field of art of this disclosure is directed to an artificial vertebral disk replacement and method.

BACKGROUND OF THE INVENTION

The spinal column is a biomechanical structure composed primarily of ligaments, muscles, vertebrae and intervertebral disks. The biomechanical functions of the spine include: (1) support of the body, which involves the transfer of the weight and the bending movements of the head, trunk and arms to the pelvis and legs, (2) complex physiological motion between these parts, and (3) protection of the spinal cord and nerve roots.

As the present society ages, it is anticipated that there will be an increase in adverse spinal conditions which are characteristic of aging. For example, with aging comes an increase in spinal stenosis (including, but not limited to, central canal and lateral stenosis), and facet joint degeneration. Spinal stenosis typically results from the thickening of the bones that make up the spinal column and is characterized by a reduction in the available space for the passage of blood vessels and nerves. Facet joint degeneration results from the constant load borne by the facet joints, and the eventual wear that results. Pain associated with both conditions can be relieved by medication and/or surgery.

In addition to spinal stenosis and facet joint degeneration, the incidence of damage to the intervertebral disks is also common. The primary purpose of the intervertebral disk is to act as a shock absorber. The disk is constructed of an inner gel-like structure, the nucleus pulposus (the nucleus), and an outer rigid structure comprised of collagen fibers, the annulus fibrosus (the annulus). At birth, the disk is 80% water which then gradually diminishes with time, thereby becoming stiff. With age, disks may degenerate, and bulge, thin, herniate, or ossify. Additionally, damage to disks may occur as a result disease, trauma or injury to the spine.

The damage to disks may call for a range of restorative procedures. If the damage is not extensive, repair may be indicated, whereas extensive damage may indicate full replacement. Regarding the evolution of restoration of damage to intervertebral disks, rigid fixation procedures resulting in fusion are still the most commonly performed surgical intervention. However, trends suggest a move away from such procedures. Currently, areas evolving to address the shortcomings of fusion for remediation of disk damage include technologies and procedures that preserve or repair the annulus, that replace or repair the nucleus, and that advance implants for total disk replacement. The trend away from fusion is driven both by issues concerning the quality of life for those suffering from damaged intervertebral disks, as well as responsible health care management. These issues drive the desire for procedures that are minimally invasive, can be tolerated by patients of all ages, especially seniors, and can be performed preferably on an out-patient basis.

Most recently, there has been an increased interest in total disk replacement technology. A number of artificial disks are beginning to appear in the medical device marketplace. These artificial disks vary greatly in shape, design and functionality. With these devices are available tools and methods for insertion of the devices between the vertebrae.

Accordingly, there is a need in the art for innovation in technologies and methods that advance the art in the area of minimally invasive intervertebral disk replacement. This not only enhances the quality of life for those suffering from the condition, but is responsive to the current needs of health care management.

DETAILED DESCRIPTION OF THE PRESENT INVENTION

The following description is presented to enable any person skilled in the art to make and use the implant of the present invention. Various modifications to the embodiments described will be readily apparent to those skilled in the art, and the principles defined herein can be applied to other embodiments and applications without departing from the spirit and scope of what is disclosed and defined by the appended claims. Thus, what is disclosed is not intended to be limited to the embodiments shown, but is to be accorded the widest scope consistent with the principles and features disclosed herein. To the extent necessary to achieve a complete understanding of what is disclosed herein, the specification and drawings of all patents and patent applications cited in this application are incorporated herein by reference.

Figure 1A:
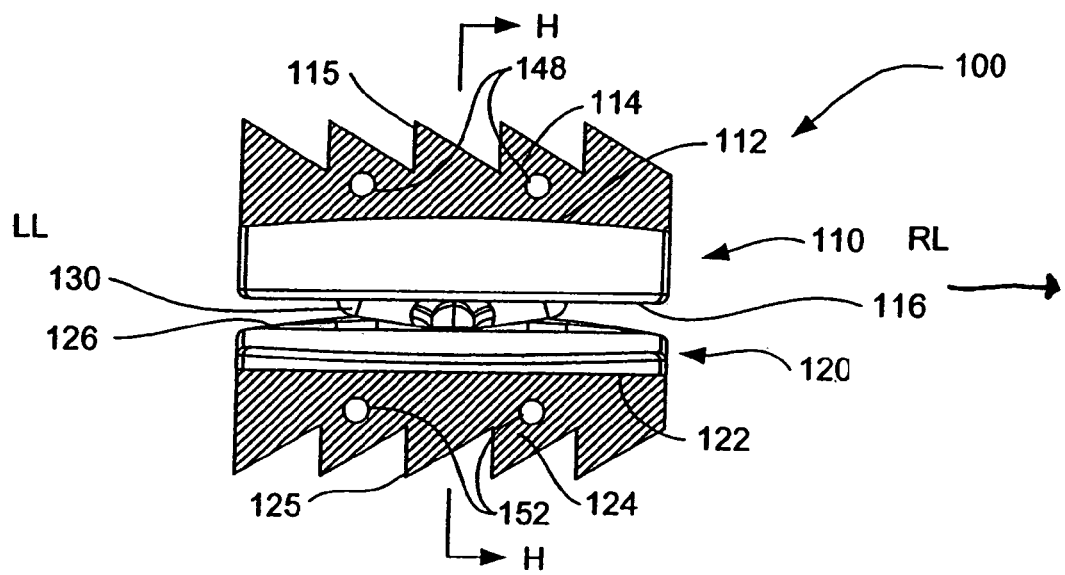
FIG. 1A is a front view of an embodiment of the disclosed implant.
Figure 1B:
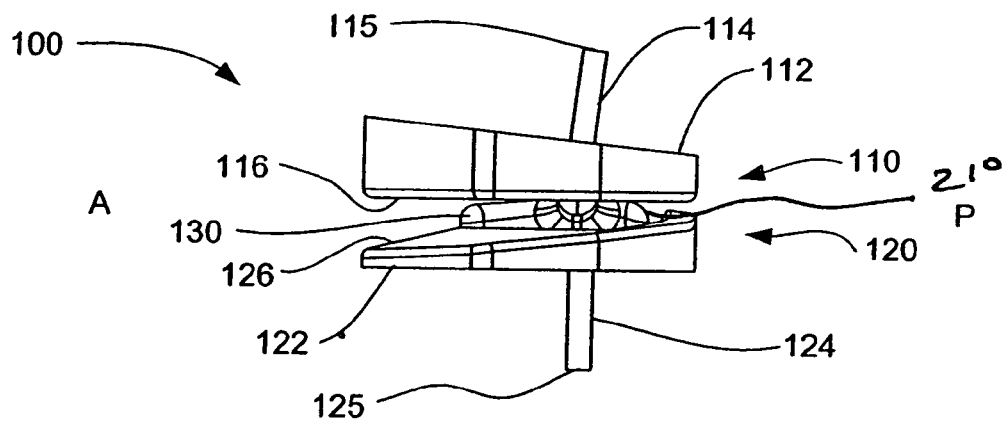
FIG. 1B is a side view of an embodiment of the disclosed implant.
Figure 1C:
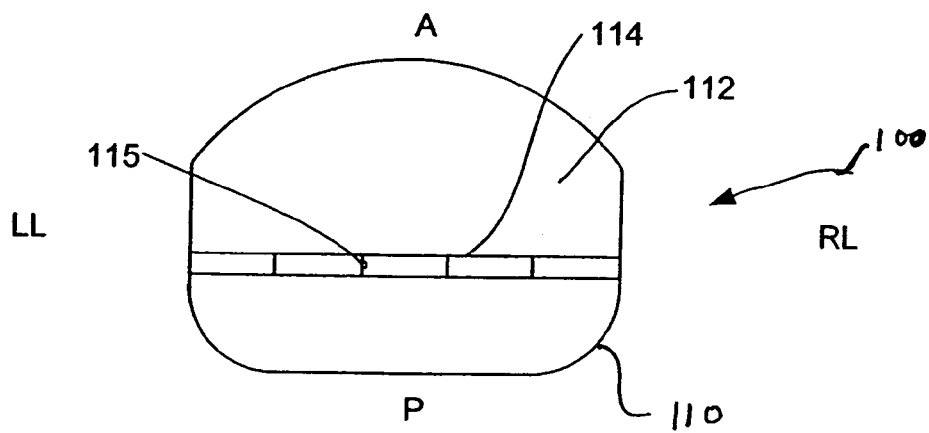
FIG. 1C is a top view of an embodiment of the disclosed implant.

FIG. 1A shows a front view of an embodiment of the implant 100. The designations, "A" for anterior, "P" for posterior, "RL" for right lateral, and "LL" for left lateral are given in the drawings for spatial directional orientation. These designations give the relationship of all faces or ends of the implant with respect to the superior perspective; i.e. looking down the axis of the spine. As shown in the Figures, the implant 100 has an anterior side A, a posterior side P, and two lateral sides, LL and RL which extend between the anterior side A and the posterior side P. The anterior side A faces the anterior direction when the implant 100 is inserted into the spine. The posterior side P faces the posterior direction when the implant 100 is inserted into the spine. The right lateral side RL faces the lateral direction away from the right side of the spine, whereas the left lateral side LL faces the lateral direction away from the left side of the spine when the implant 100 is inserted therein. In one embodiment, as shown in FIG. 1C, the implant 100 has a perimeter shape which is configured to correspond to the perimeter shape of the vertebral disks, whereby the anterior side A is curved and the posterior side P is parallel to the sagittal plane. In another embodiment, the implant 100 has a perimeter shape which does not contour to the shape of the vertebral disks. As will be appreciated by those of ordinary skill in the art, the perimeter shape of the upper end plate 110 and the lower end plate 120 can be the same or different from one another.

The implant 100 preferably includes an upper end plate 110 that is configured to mate with an upper vertebral body. The implant 100 preferably includes a lower end plate 120 that is configured to mate with a lower vertebral body. The implant 100 also includes a spacer 130 positioned between the upper end plate 110 and the lower end plate 120. The spacer 130 separates the upper end plate 110 from the lower end plate 120 and also facilitates pivotal and/or rotational as well as twisting movement of the upper end plate 110 and the lower end plate 120 relative to each other and the spacer 130. The spacer 130 is preferably in the form of a crossbar as discussed in more detail below.

Figure 4:
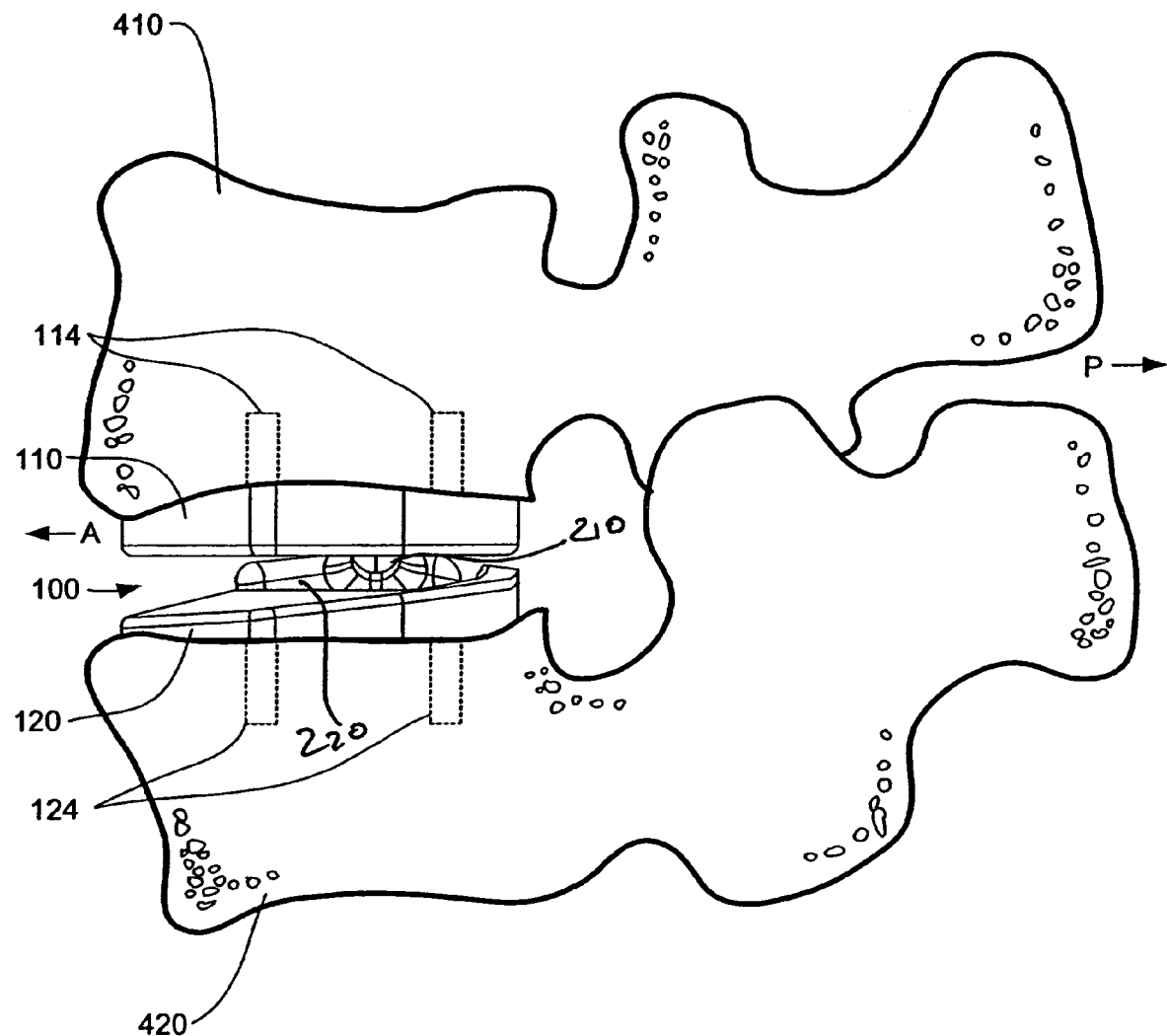
FIG. 4 is a side view of an embodiment of the disclosed implant implanted between adjacent vertebral bodies.

The upper end plate 110 has a first outer surface 112 which comes into contact and mates with the underside of the upper vertebral body. The implant 100 includes a first keel 114, as shown in FIGS. 1A-1C, which preferably extends away from the first outer surface 112 in a direction substantially perpendicular to the first outer surface 112. In one embodiment, when the implant 100 is inserted between the vertebral bodies, the first keel 114 preferably extends into a keel receiving channel which is cut into the underside of the upper vertebral body to anchor the upper end plate 110 thereto. The first keel 114 extends longitudinally across the first outer surface 112 between the left lateral side LL and the right lateral side RL, as shown in FIG. 1C. The first keel 114 is thus oriented to be substantially perpendicular to the sagittal plane of the spine, which is known to one skilled in the art as the plane which traverses from the posterior toward the anterior of the patient or patient's spine. As shown in FIG. 1C, it is preferred that the right lateral side RL and left lateral side LL of the implant 100 are parallel to the sagittal plane. In a preferred embodiment, the first keel 114 is oriented to be substantially parallel to the coronal plane of the spine which is known in the art as the plane that is parallel to the patient's shoulders. In another embodiment, the first keel 114 extends longitudinally only partially across the first outer surface 112. It should be noted that although one keel 114 is shown laterally across the first outer surface 112 in FIG. 1C, more than one keel 114 is alternatively disposed on the first outer surface 112, as shown in FIG. 4. It is contemplated that the plurality of keels 114, as shown in FIG. 4, are parallel to each other and are perpendicular to the sagittal plane of the spine, although not necessarily. Although the implant of the present invention is shown and described herein as having one or more keels laterally oriented between the right and left lateral sides, the implant described herein can alternatively have keels which are oriented between the anterior and posterior sides as described in U.S. patent application Ser. No. 10/684,668 which is incorporated by reference.

It is preferred that the first keel 114 of the upper end plate 110 includes a plurality of teeth 115. In one embodiment, the teeth 115 of the keel 114 are angled and point towards the left lateral face of the implant 100, as shown in the example in FIG. 1A. The left angled teeth 115 allow the upper end plate 110, as shown in FIG. 1A, to be easily inserted between the vertebral bodies from a left lateral approach. This is so, because the angled configuration of the teeth 115 provide little frictional resistance against the underside of the vertebral body when inserted into the spine. The angled configuration of the teeth 115 also prevents the upper end plate 110 from becoming dislodged or unintentionally slipping out of the spine after being inserted therein. In another embodiment, the teeth 115 of the keel 114 are angled and point towards the right lateral face RL of the implant 100, opposite of that shown in the embodiment in FIG. 1A. This configuration allows the upper end plate 110 to be easily inserted into the spine from a right lateral side approach.

Figure 3:
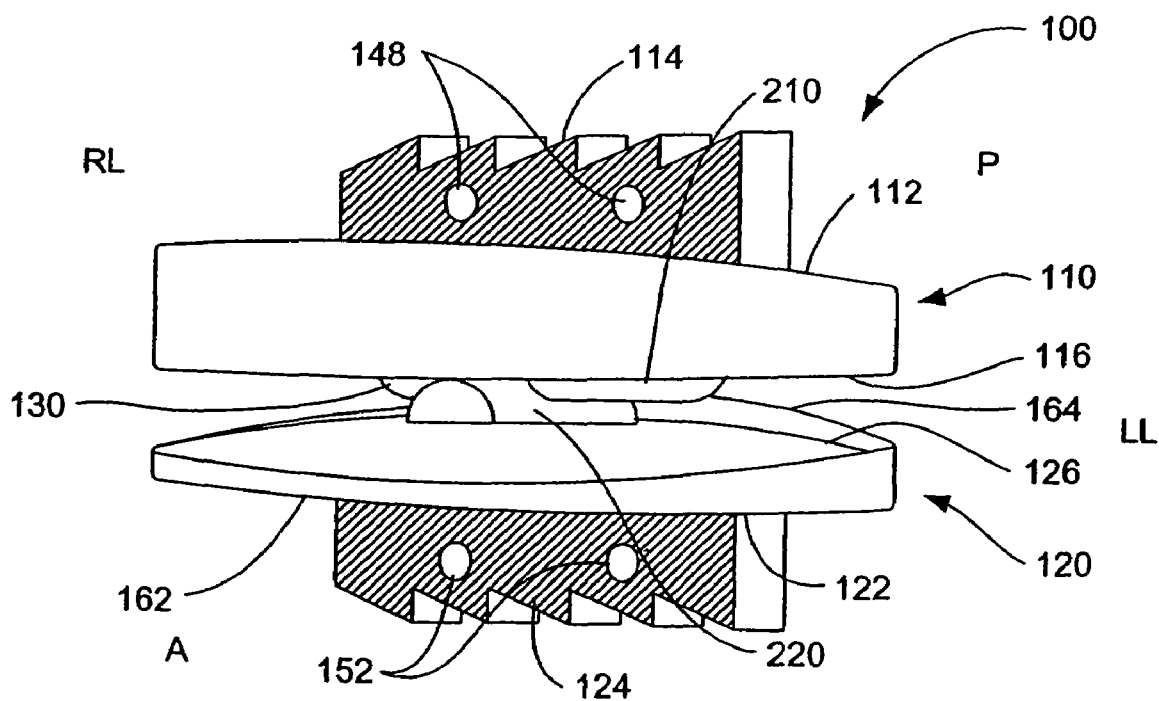
FIG. 3 is a perspective view of the assembled implant of an embodiment of the present invention.

The lower end plate 120 of the present implant 100 includes a second outer surface 122, as shown in FIGS. 1A and 1B. The second outer surface 122 preferably comes into contact with and mates with the top-side of the lower vertebral body. The implant 100 includes a second keel 124, as shown in FIGS. 1A and 1B, which preferably extends away from the second outer surface 122 in a direction substantially perpendicular to the second outer surface 122. In one embodiment, when the implant 100 is inserted between the vertebral bodies, the second keel 124 preferably extends into a keel receiving channel in the top-side of the lower vertebral body to anchor the lower end plate 120 thereto. The second keel 124 extends longitudinally across the second outer surface 122 between the left lateral side LL and the right lateral side RL, as shown in FIG. 3. In another embodiment, the second keel 124 extends longitudinally only partially across the second outer surface 122. The second keel 124 is thus oriented to be substantially perpendicular to the sagittal plane of the spine. In a preferred embodiment, the second keel 124 is oriented to be substantially parallel to the coronal plane of the spine. It should be noted that although one keel 124 is shown laterally across the second outer surface 122 in FIG. 3, more than one keel 124 is alternatively disposed on the second outer surface 122, as shown in FIG. 4. It is contemplated that the plurality of keels 124, as shown in FIG. 4, are parallel to each other and are perpendicular to the sagittal plane of the spine.

It is preferred that the second keel 124 of the lower end plate 120 includes a plurality of teeth 125. In one embodiment, the teeth 125 of the keel 124 are angled and face towards the left lateral face of the implant 100, as shown in the example in FIG. 1A. The left angled teeth 125 allow the lower end plate 120, as shown in FIG. 1A, to be easily inserted between the vertebral bodies from a left lateral approach. This is so, because the angled configuration of the teeth 125 provide little frictional resistance against the top-side of the vertebral body when inserted into the spine. The angled configuration of the teeth 125 also prevents the lower end plate 120 from becoming dislodged or unintentionally slipping out of the spine after being inserted therein. In another embodiment, the teeth 125 of the keel 124 are angled and point towards the right lateral face RL of the implant 100, opposite of that shown in the embodiment in FIG. 1A. This configuration allows the lower end plate 120 to be easily inserted into the spine from a right lateral side approach.

In the embodiment shown in FIG. 1A, the first and second keels 114,124 preferably include ports 148, 152 therethrough. The ports 148, 152 facilitate bone in-growth, wherein bone from the vertebral bodies can grow thorough the ports 148,152 to aid in securing the first and second keels 114, 124, and thus the implant 100 to the spine. In one embodiment the outer surfaces of the first and second keels 114,124 and the first and second outer surfaces 112, 122 of the implant 100 are roughened in order to promote bone in-growths into the defined roughened surfaces of the implant 100. In one embodiment, the first and second keels 114,124, and the first and second outer surfaces 112, 122 of implant 100 are coated with one or more materials that promote bone growth. Such materials include, but are not limited to, bone morphogenic protein (BMP) and hyaluronic acid. Other substances which promote bone growth relative to and into the keel, keel ports, and other external surfaces of the implant 100 are contemplated.

The first and second keels 114, 124 preferably extend between the vertebral bodies to anchor the implant 100 to the spine. The lateral orientation of the first keel 114 and the second keel 124 allow the implant 100 to be inserted into the spine using a lateral approach as opposed to an anterior or posterior approach, which is advantageous, because the spinal nerves in the spinal cavity are minimally undisturbed when the implant 100 is inserted laterally. In comparison to a posterior insertion approach in which the spinal nerves can be substantially disturbed, the spinal nerves are bypassed and relatively undisturbed when the implant 100 is inserted laterally between the vertebral bodies from the side of the spine. Although an anterior insertion approach has its benefits, the lateral insertion approach can allow the present implant 100, and associated implantation tools, to be inserted into the spine with less disturbance of the patient's internal organs. This can translate into less time and risk associated with preparing the spine for insertion as well as inserting the implant itself into the spine. Further, the laterally oriented first and second keels 114, 124 offer substantial stability to the vertebral bodies during extension, flexion and lateral bending of the spine.

Figure 1D:
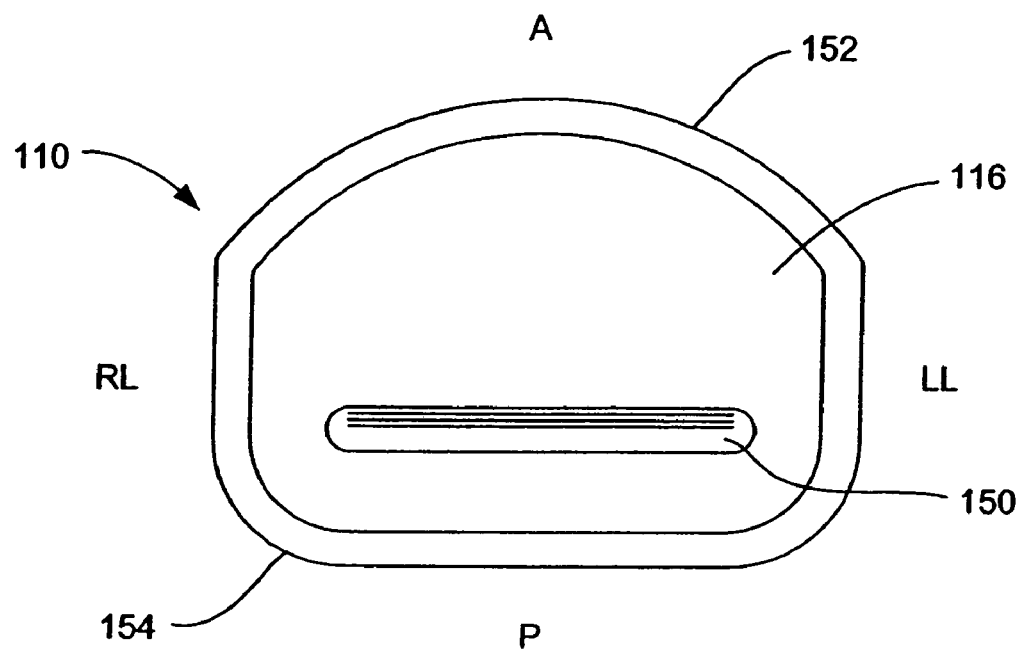
FIG. 1D is a plan view of an embodiment of the first inner surface of the upper end plate of the disclosed implant.
Figure 1E:
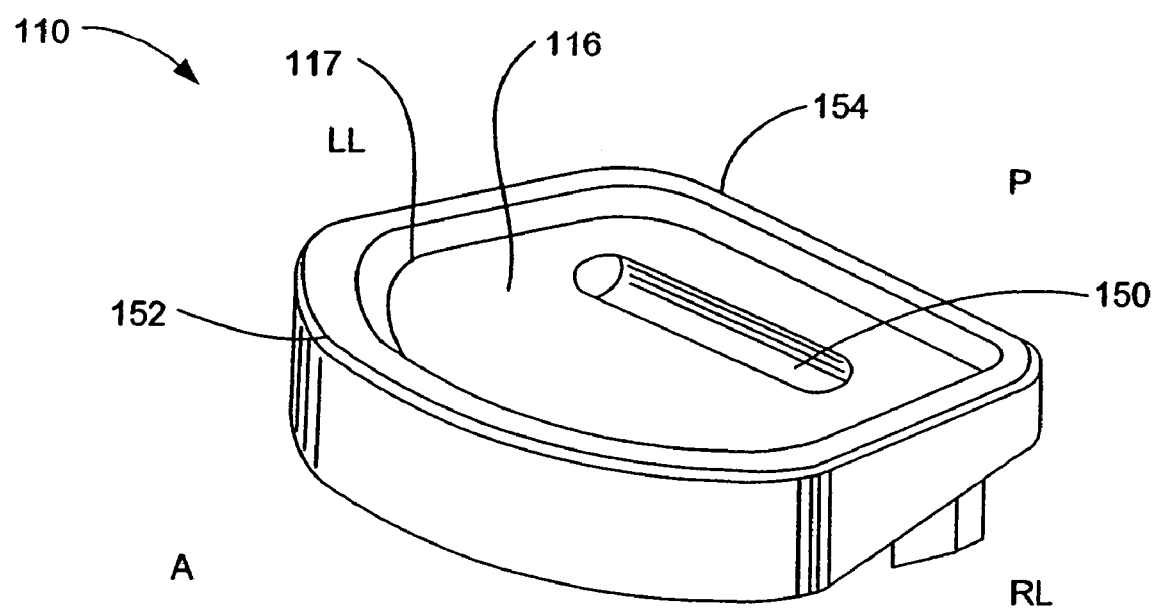
FIG. 1E is a perspective view of an embodiment of the upper end plate of the disclosed implant.

As shown in FIGS. 1D and 1E, the upper end plate 110 includes a first inner surface 116. It should be noted that the upper end plate 110 is shown oriented upside down in FIGS. 1D and 1E, whereby the inner surface 116 is shown facing upwards. The first inner surface 116 receives and engages the spacer 130 of the implant and opposes an inner surface 126 (FIG. 1B) of the second end plate 120. In one embodiment, the first inner surface 116 is designed to form a planar surface that is parallel with the first outer surface 112. In another embodiment, the first inner surface 116 is designed to form a planar surface that is non-parallel with the first outer surface 112. In particular, as shown in FIGS. 1B and 1E, the anterior side A of the end plate 110 has a larger thickness (i.e. distance between the first outer side 110 and first inner side 116) than the thickness of the posterior side P.

As shown in FIGS. 1D and 1E, the first inner surface 116 of the upper end plate 110 preferably includes a channel, also referred to as a socket, 150 therein. As will be discussed below, the spacer includes a spacer beam, wherein at least a portion of the spacer beam can be seated in the channel 150 to allow the first and/or second end plates of the assembled implant 100 to pivot or rotate relative to each other. As shown in FIGS. 1D and 1E, the channel 150 is preferably concave and extends lengthwise between the left lateral side LL and the right lateral side RL of the upper end plate 110. Alternatively, the channel 150 extends lengthwise between the anterior side A and the posterior side P of the upper end plate 110. In one embodiment, as shown in FIG. 1E, the upper end plate 110 includes a ridge 117 formed in the first inner surface 116, whereby the ridge 117 is surrounded by the first inner surface 116, which is raised relative thereto. In one embodiment, the channel 150 receives a portion of the spacer beam. In another embodiment, the spacer beam fits within the channel 150.

Figure 1F:
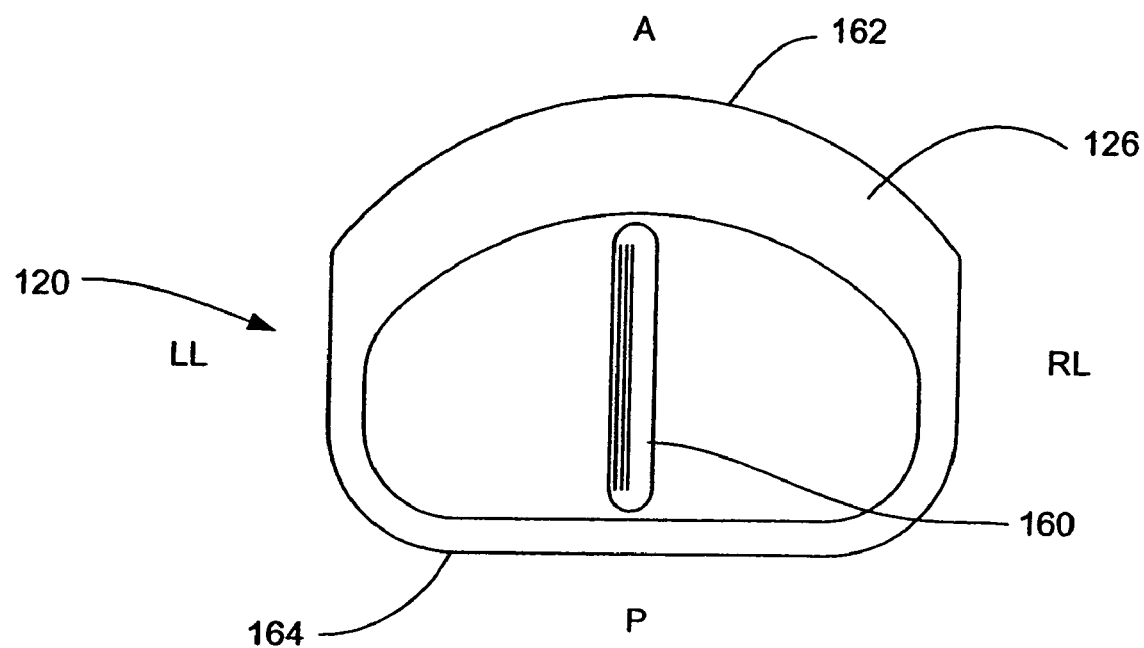
FIG. 1F is a plan view of the second inner surface of the lower end plate of an embodiment of the disclosed implant.
Figure 1G:
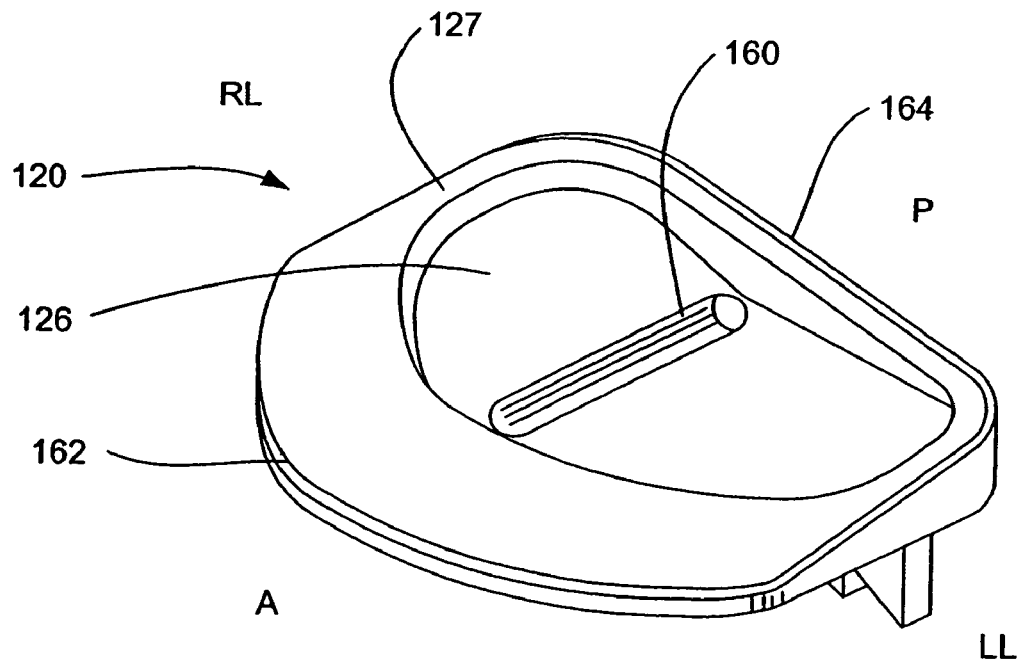
FIG. 1G is a perspective view of the lower end plate of an embodiment of the disclosed implant.

As shown in FIGS. 1F and 1G, the lower end plate 120 includes a second inner surface 126. The second inner surface 126 receives and engages the spacer 130 of the implant and opposes the inner surface 126 (FIG. 1E) of the first end plate 110. In one embodiment, the second inner surface 126 is designed to form a planar surface that is parallel to the second outer surface 122. In another embodiment, the second inner surface 126 is designed to form a planar surface that is non-parallel to the first outer surface 122. In particular, as shown in FIGS. 1G and 1E, the anterior side A of the end plate 120 has a smaller thickness (i.e. distance between the second outer side 120 and second inner side 126) than the thickness of the posterior side P.

Figure 1H:
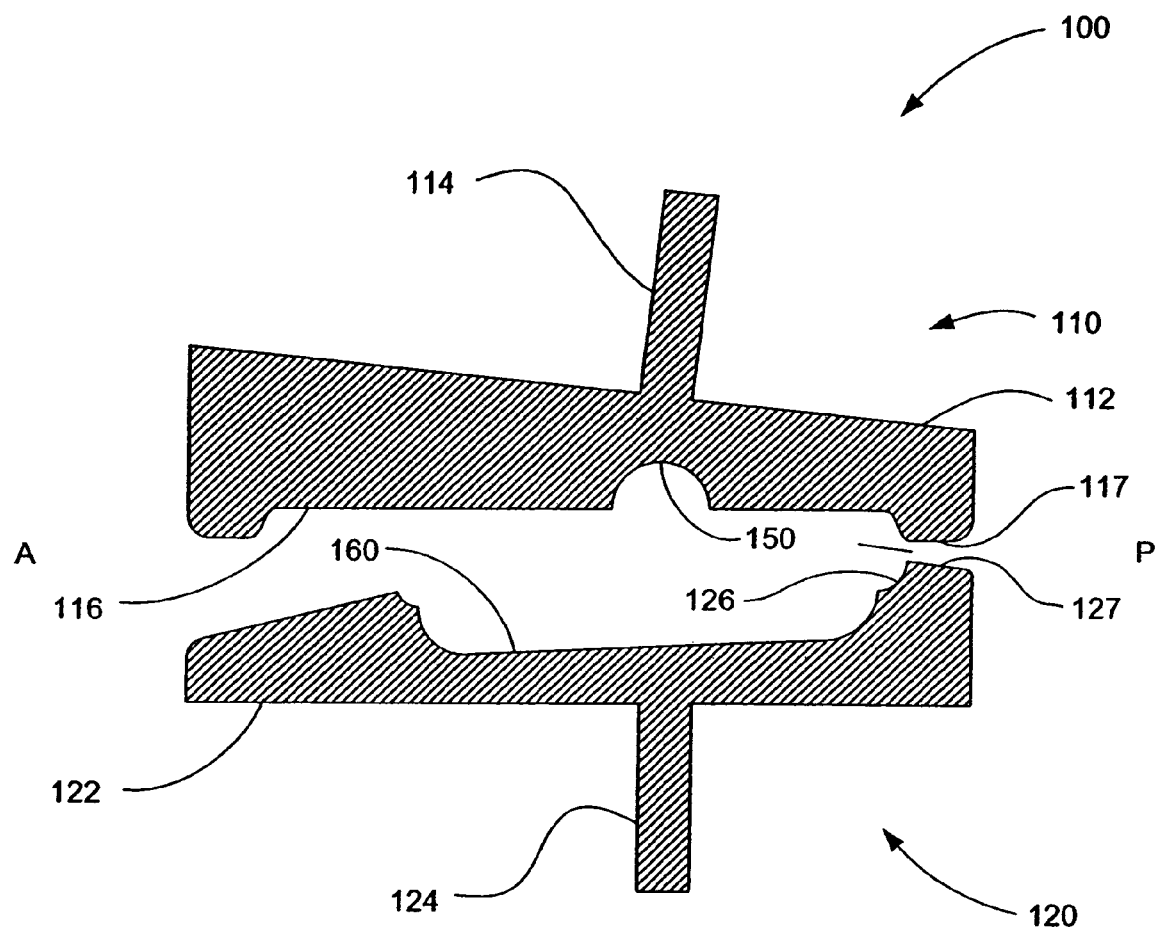
FIG. 1H is a cross-sectional view of the upper and lower end plates of the implant taken along line H-H in FIG. 1A.

As shown in FIGS. 1G and 1H, the second inner surface 126 of the lower end plate 120 preferably includes a channel, also referred to as a socket, 160 therein. As will be discussed below, the spacer 130 includes a spacer beam which can be placed into the channel 160 in order to allow the first and/or second end plates of the assembled implant to pivot or rotate relative to each other. As shown in FIGS. 1G and 1H, the channel 160 is preferably concave and extends lengthwise between the anterior side A and the posterior side P of the lower end plate 120. Alternatively, the channel 160 extends lengthwise between the left lateral side LL and the right lateral side RL of the lower end plate 120. In one embodiment, as shown in FIG. 1G, the lower end plate 120 includes a ridge 127 formed in the second inner surface 126, whereby the ridge 127 is surrounded by the second inner surface 126, which is raised relative thereto. In one embodiment, the channel 160 receives a portion of the spacer beam. In another embodiment, the spacer beam fits within the channel 160.

In one embodiment, the first outer surface 112 of the first end plate 110 is substantially parallel to the second outer surface 122 of the second end plate 120 when the implant 100 is assembled and is in a neutral position (i.e., the position where the first end plate 110 has not rotated relative to the second end plate 120). Alternatively, the first outer surface 112 of the first end plate 110 is non-parallel to the planar surface of the second outer surface 122 of the second end plate 120 when the implant 100 is assembled and in the neutral position. The non-parallel orientation of the first end plate 110 and the second end plate 120 allows the plates to pivot a greater degree with respect to each other. Additionally, other factors such as the height of the spacer 130 and the position of the keel receiving channels can be adjusted in order to increase the degree by which the first end plate 110 and the second end plate 120 can pivot relative to each other and the spacer 130.

FIG. 1H illustrates a cross-section of the implant 100 taken along the lines H-H of FIG. 1A. As shown in FIG. 1H, the first inner surface 116 of the first plate 110 substantially opposes the second inner surface 126 of the second plate 120. In addition, FIG. 1H illustrates the first channel 150 located in the first inner surface 116 which extends laterally between the left lateral side LL and the right lateral side RL. Additionally, the second channel 160 is located in the second inner surface 126 and extends between the anterior side A and the posterior side P, as shown in FIG. 1H.

In one embodiment, the planar surfaces which correspond to the first and second outer surfaces 112, 122 of the implant lie parallel or substantially parallel to the axial plane of the body when the implant 100 is inserted between adjacent vertebrae. In one embodiment, the planar surfaces which correspond to the first and second inner surfaces 116, 126 of the first and second end plates 110, 120 lie parallel, or substantially parallel, to the axial plane of the body when the implant is implanted. In one embodiment, the outer surfaces 112, 122 and the inner surfaces 116, 126 both lie parallel or substantially parallel to the axial plane of the body when the implant is implanted. In each of the embodiments, either or both keels 114, 124 are perpendicular to the sagittal plane. Preferably, the keels 114, 124 are also parallel to the coronal plane of the body.

Figure 2A:
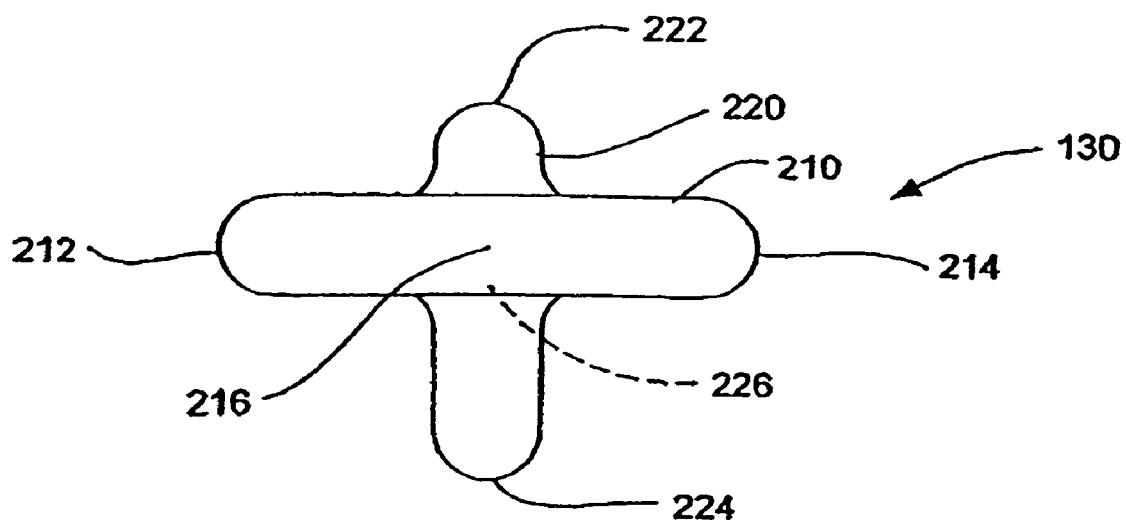
FIG. 2A is a top view of a crossbar of an embodiment of the disclosed implant.

FIG. 2A illustrates a top view of the preferred crossbar spacer 130 of the present invention. The crossbar spacer 130 preferably has a first spacer beam 210 and a second spacer beam 220 as shown in FIG. 2A, whereby the first spacer beam 210 is oriented perpendicular to the second spacer beam 220. The first spacer beam 210 has a first end 212 and a second opposed end 214 as well as a midpoint 216 therebetween. The second spacer beam 220 has a first end 222 and a second opposed end 224 as well as a midpoint 226 therebetween. As shown in the figures, the spacer beams 210, 220 are preferably circular in cross section, although other appropriate shapes are contemplated.

In the embodiment shown in FIG. 2A, the midpoint 216 of the first spacer beam 210 is not aligned with the midpoint 226 of the second spacer beam 220. Instead, the midpoint 216 of the first spacer beam is proximal to the first end 222 and distal to the second end 224 of the second spacer beam 220. In this configuration, the first and second beams 210, 220 substantially form a cross or "T" shape.

in another embodiment, the first beam 210 can be positioned transversely along the length of the second beam 220 such that the midpoint 216 of the first beam 210 and the midpoint 226 of the second beam 220 are aligned with one another. Where both beams 210, 220 are positioned at the respective midpoints 216, 226, the crossbar spacer 130 substantially forms a plus sign, "+".

Figure 2B:
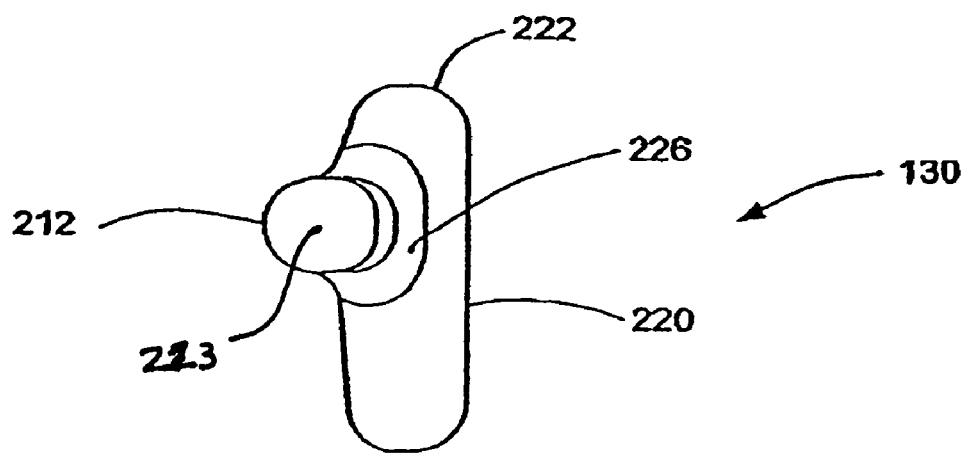
FIG. 2B is a side view of the crossbar of an embodiment of the disclosed implant.
Figure 2C:
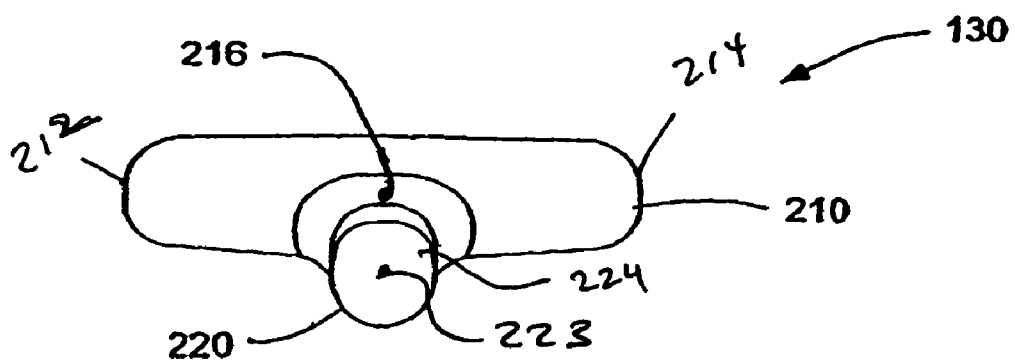
FIG. 2C is a bottom view of the crossbar of an embodiment of the disclosed implant.
Figure 2D:
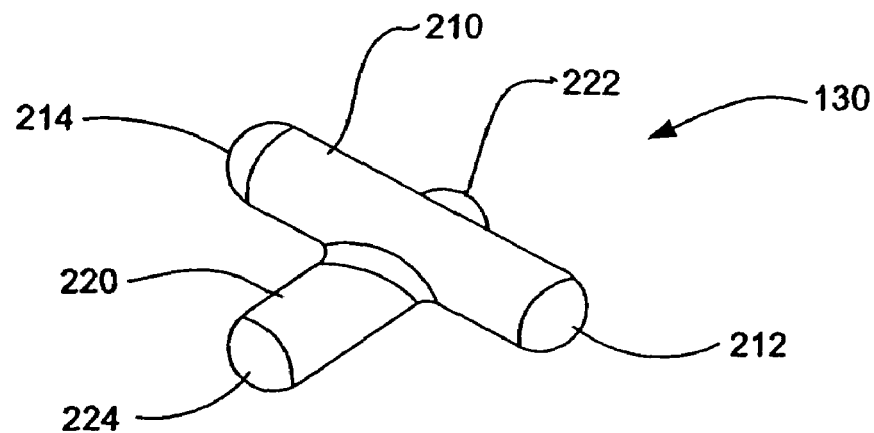
FIG. 2D is a perspective view of the crossbar of an embodiment of the disclosed implant.

FIG. 2B shows a side view of the crossbar spacer 130 of the implant 100. As is apparent from FIG. 2B, the first beam 210 is oriented such that the center 213 of the first beam 210 is off-set from the center 223 (FIG. 2C) of the second beam 220. Thus, the first beam 210 is located along a plane which is parallel and adjacent to a plane along which the second beam 220 is oriented. Similarly, as shown in FIG. 2C, the second beam 220 is oriented such that the center 223 of the first beam 220 is off-set from the center 213 of the first beam 210. The off-set positioning of the first beam 210 and the second beam 220 allows the spacer 130 to be positioned between, and in contact with, the upper end plate 110 and the lower end plate at the same time. Additionally, the off-set positioning of the beams 210, 220 allow the upper and lower end plates 110, 120 to pivot about the beams of the spacer 130 to accommodate flexion, extension, twisting and/or lateral bending of the spine.

In constructing the crossbar 130, the first beam 210 can be formed integrally with the second beam 220 to be unitary in construction. Alternatively, the first beam 210 can be adhered to the second beam 220 using any other suitable method (e.g. spot welding). It should be noted that the first beam 210 and the second beam 220, as well as the spacer 130 as a whole, are sufficiently constructed to withstand the load forces applied by the end plates 110, 120 in the neutral position as well as during flexion, extension and/or lateral bending movements. The spacer 130 can be formed by extrusion, injection, compression molding, machining or any other appropriate techniques.

Viewing FIGS. 1A, 1B and 3, an assembled embodiment of the implant 100 is depicted. The upper end plate 110 is configured to mate with the first vertebra and the lower end plate 120 is configured to mate with a second vertebra. A crossbar 130 that sits between the first end plate 110 and the second end plate 120 is also provided. As is evident from the figures, the upper beam 210 of the crossbar 130 is placed in the channel 150 of the upper end plate 110 such that the upper beam 210 is approximately parallel with the keels 114, 124.

As can be seen from FIGS. 1H and 4, the "T"-shaped spacer 130 sits between the upper and lower end plates 110, 120, wherein the first beam 210 is preferably received in the channel 150 (FIG. 1H) and the second beam 220 is preferably received in the channel 160 (FIG. 1H). As shown in FIG. 4, the first beam 210 is positioned proximal to the posterior side P rather than the anterior side A of the implant 100, whereby the first beam 210 is oriented parallel to the keels 114, 124 and perpendicular to the sagittal plane. In another embodiment, the upper beam 210 can be positioned midway between the posterior and the anterior faces of the implant 100 in the embodiment that the crossbar spacer 130 has a "+" shape. As shown in FIG. 4, the lower beam 220 is placed in the channel 160 of the lower end plate 120 such that the lower beam 220 is approximately perpendicular to the keels 114, 124 and parallel with the sagittal plane.

As stated above, the crossbar spacer facilitates pivotal or rotational movement of the first end plate 110 and the second end plate 120, relative to each other. In particular, the interface between the first beam 210 of the spacer 130 and the channel 150 allows the upper end plate 110 and/or lower end plate 120 to pivot or rotate about the first beam 210 when the patient moves backwards (extension) and forwards (flexion). Additionally, the interface between the second beam 210 of the spacer 130 and the channel 160 allows the lower end plate 120 and/or upper end plate 110 to pivot or rotate about the second beam 210 when the patient bends side to side (laterally). The patient's weight as well as gravity hold the spacer 130 securely seated within the channels 150, 160. As stated above, the implant 100 includes channels 150, 160 in one embodiment, although not necessarily.

In one embodiment, there is a loose fit between the spacer 130 and the upper and lower end plates 110,120. In particular, there is a loose fit between the upper beam 210 and the upper channel 150 and also between the lower beam 220 and the lower channel 160. This loose fit allows for a twisting motion of the upper and/or lower end plates, and thus vertebral bodies, about a vertical axis through the center of the spine.

FIG. 4 shows a side view of an implant 100 inserted between two vertebral bodies 410, 420. The implant 100 is shown inserted between the two vertebrae 410, 420 with two first keels 114 extending from the first end plate 110, and two second keels 124 extending from the second end plate 120. The first and second keels 114,124 are approximately perpendicular to the sagittal plane of the spine, and preferably straddle the point of articulation of the spacer 130. A gap is present between the first end plate 110 and the second end plate 120 at the anterior A face of implant 100 is preferably greater than at the posterior end P face of implant 100. The larger gap at the anterior face vs. the posterior face of implant 100 allows forward (flexion) movement to be facilitated to a greater degree than backward (extension) movement. Thus, in one example of a forward bending movement of up to 10° can be achieved while a backward bending movement of 5° can be achieved. Other angles are contemplated within the scope of the present invention.

In one embodiment, the implant can be made of medical grade titanium, stainless steel or cobalt chrome. The material has appropriate physical and mechanical properties and is suitable for carrying and spreading the physical load between the spinous process. Other materials that have appropriate structural strength and that are suitable for implantation into a patient can also be used. One class of materials contemplated for use in implant 100 is the class of biocompatible polymers. Copolymers, blends and composites of polymers are also contemplated for fabrication of parts of the disclosed device. A copolymer is a polymer derived from more than one species of monomer. A polymer composite is a heterogeneous combination of two or more materials, wherein the constituents are not miscible, and therefore exhibit an interface between one another. A polymer blend is a macroscopically homogeneous mixture of two or more different species of polymer.

One group of biocompatible polymers are the polyarylesterketones which has several members, which include polyetheretherketone (PEEK), and polyetherketoneketone (PEKK). PEEK has proven as a durable material for implants, as well as meeting criteria of biocompatibility. Medical grade PEEK is available from Victrex Corporation under the product name PEEK-OPTIMA. Medical grade PEKK is available from Oxford Performance Materials under the name OXPEKK, and also from CoorsTek under the name Bio-PEKK. Other materials that can be used include polyetherketone (PEK), polyetherketoneether-ketoneketone (PEKEKK), and polyetheretherketoneketone (PEEKK), and, generally, a polyaryletheretherketone. Further, other polyketones can be used as well as other thermoplastics.

Reference to appropriate polymers that can be used in the spacer can be made to the following documents, all of which are incorporated herein by reference. These documents include: PCT Publication WO 02/02158 A1, dated Jan. 10, 2002, entitled "Bio-Compatible Polymeric Materials;" PCT Publication WO 02/00275 A1, dated Jan. 3, 2002, entitled "Bio-Compatible Polymeric Materials;" and, PCT Publication WO 02/00270 A1, dated Jan. 3, 2002, entitled "Bio-Compatible Polymeric Materials."

Still another interesting group of biocompatible polymers are polyalkyl biocompatible polymers, such as polyethylenes, polypropylenes, and the like. These medical grade biocompatible polymers are also available as reinforced polymer materials. To reinforce a polymeric material, fillers, are added to a polymer, copolymer, polymer blend, or polymer composite. Fillers are added to modify properties, such as mechanical, optical, and thermal properties. In this case, fillers, such as carbon fibers, are added to reinforce the polymers mechanically to enhance strength for certain uses, such as load bearing devices.

For example, other grades of PEEK are also available and contemplated, such as 30% glass-filled or 30% carbon-filled, provided such materials are cleared for use in implantable devices by the FDA, or other regulatory body. Glass-filled PEEK reduces the expansion rate and increases the flexural modulus of PEEK relative to that which is unfilled. The resulting product is known to be ideal for improved strength, stiffness, or stability. Carbon-filled PEEK is known to enhance the compressive strength and stiffness of PEEK and lower its expansion rate. Carbon-filled PEEK offers wear resistance and load carrying capability.

Alternatively, the spacer 130 can be made out of a polymer, and more specifically, the polymer is a thermoplastic with the other components made of the materials specified above. Still more specifically, the material is PEEK 450G, which is an unfilled PEEK approved for medical implantation available from Victrex of Lancashire, Great Britain. (Victrex is located at www.matweb.com or see Boedeker www.boedeker.com). Other sources of this material include Gharda located in Panoli, India (www.ghardapolymers.com). Further in this embodiment, the PEEK has the following additional approximate properties:

| Property | Value |
| --- | --- |
| Density | 1.3 g/cc |
| Rockwell M | 99 |
| Rockwell R | 126 |
| Tensile Strength | 97 Mpa |
| Modulus of Elasticity | 3.5 Gpa |
| Flexural Modulus | 4.1 Gpa |

Figure 5:
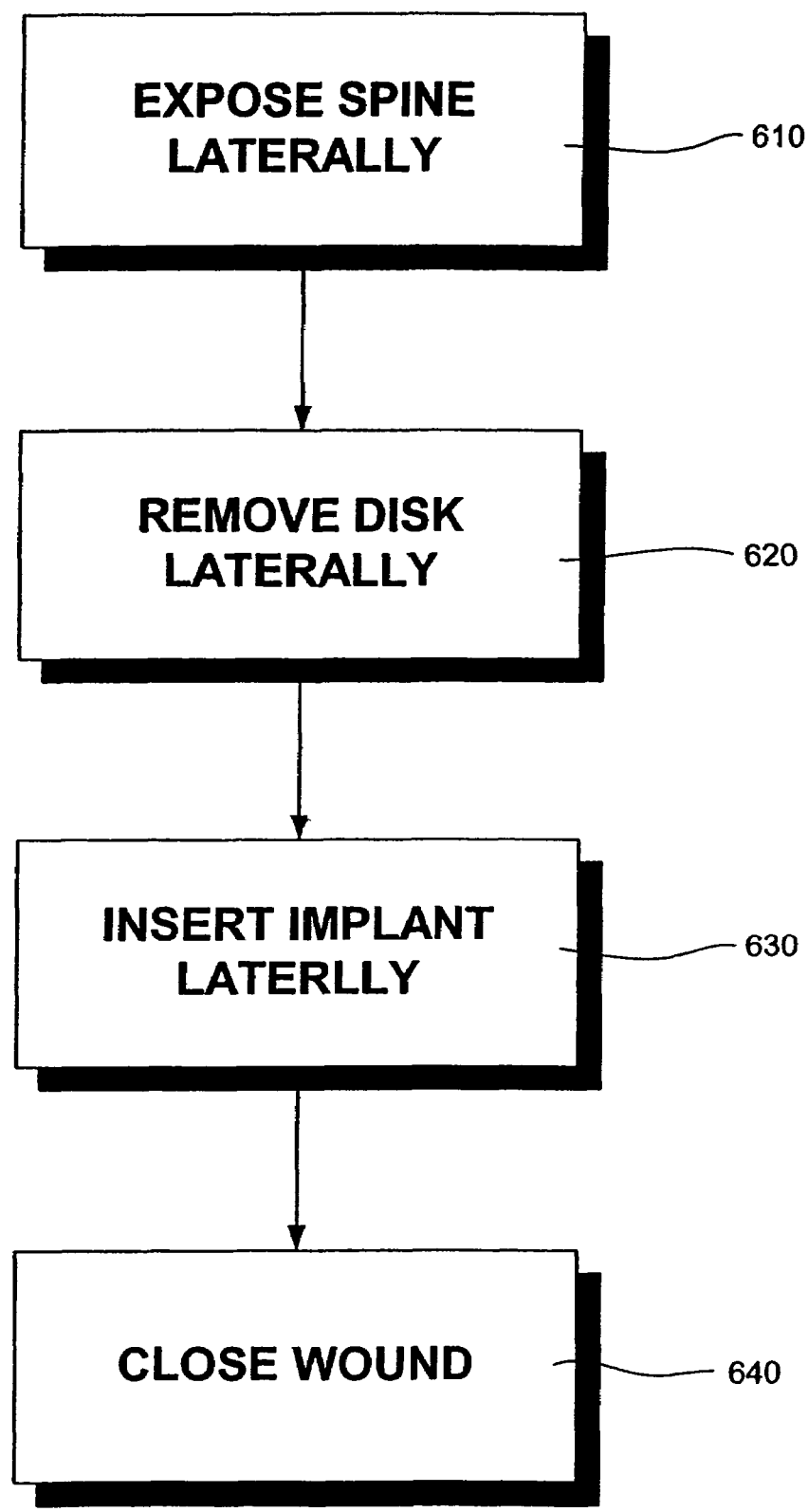
FIG. 5 is a block diagram showing the method of the lateral implantation of an embodiment of the disclosed the disclosed implant.

FIG. 5 is a block diagram showing the basic steps of the method of laterally inserting the implant 100. First the spine is exposed through a lateral access 610. The intervertebral disk is then removed laterally 620, if necessary. Following, the implant 100 is inserted laterally 630 between the adjacent vertebral bodies. Finally, the wound is closed 640. Additionally, the method includes preparing the spine for the implant by cutting channels into the vertebral bodies to accept the keels of the plates. In one embodiment, the method includes assembling the implant by inserting the crossbar spacer between the upper and lower end plates prior to installation. In one embodiment, the upper and lower end plates can be attached individually to the vertebral bodies and then assembled with the spacer to form the entire implant assembly thereafter.

What has been disclosed herein has been provided for the purposes of illustration and description. It is not intended to be exhaustive or to limit what is disclosed to the precise forms described. Many modifications and variations will be apparent to the practitioner skilled in the art. What is disclosed was chosen and described in order to best explain the principles and practical application of the embodiments described herein, thereby enabling others skilled in the art to understand the various embodiments and various modifications that are suited to the particular use contemplated. It is intended that the scope of what is disclosed be defined by the following claims and their equivalence.

What is claimed:

1. An intervertebral implant comprising:
   a. an articulating unit adapted to be inserted between adjacent vertebral bodies, the articulating unit having an outer perimeter, and having a first arcuate channel therein, the first arcuate channel having ends spaced inwardly from the first outer perimeter;
   b. a crossbar spacer in contact with the first arcuate channel, wherein the crossbar spacer and the first arcuate channel allow the articulating unit to rotate in association with flexion and extension of at least one of the vertebral bodies, wherein the crossbar spacer includes
      i. a first spacer beam having a curved outer side surface centered about a first longitudinal axis and having a first end and a second end; and
      ii. a second spacer beam perpendicular to the first spacer beam having a curved outer side surface centered about a second longitudinal axis, the first spacer beam being disposed relative to the second spacer beam so that the second longitudinal axis is closer to the first end of the first beam than to the second end, the first and second spacer beams each respectively extending beyond opposing sides of each other; and
   c. a first keel adapted to mate with a vertebral body, the first keel extending from a first outer surface of the articulating unit and oriented to be substantially parallel with the first channel.

2. The implant of claim 1 wherein the first keel further comprises a plurality of teeth.

3. The implant of claim 1 further comprising a second keel extending from a second outer surface of the articulating unit, the second keel oriented substantially parallel with the first channel.

4. The implant of claim 3 wherein the first keel further comprises a plurality of teeth.

5. The implant of claim 1 wherein the articulating unit further comprises a second channel therein to receive the crossbar spacer wherein the crossbar spacer and the second channel allow the articulating unit to rotate in association with lateral bending of at least one of the vertebral bodies.

6. The implant of claim 5 wherein the first spacer beam is in contact with the first channel in the articulating unit; and the second spacer beam is in contact with the second channel.

7. The implant of claim 1 wherein the first keel is oriented substantially perpendicular to the sagittal plane of the vertebral body.

8. An implant adapted to be inserted between adjacent vertebral bodies in a spine comprising:
   a. a first end plate having a first inner surface having a first outer perimeter, the first inner surface having a first recessed arcuate channel formed therein, the first recessed arcuate channel having ends spaced inwardly from the first outer perimeter, and the first end plate having a first keel on a first outer surface, wherein the first keel is oriented substantially parallel to the coronal plane of the spine;
   b. a second end plate having a second inner surface opposed to the first inner surface, the second inner surface having a second outer perimeter, the second inner surface having a second recessed arcuate channel formed therein, the second recessed arcuate channel having ends spaced inwardly from the second outer perimeter, and the second end plate having a second keel on a second outer surface, wherein the second keel is oriented substantially parallel to the first keel; and
   c. a spacer having a first spacer member in contact with the first inner surface and a second spacer member in contact with the second inner surface and oriented perpendicular to the first spacer member, wherein the first spacer member includes a curved outer side surface centered about a first longitudinal axis and having a first end and a second end, and the second spacer member includes a curved outer side surface centered about a second longitudinal axis, the first spacer member being disposed relative to the second spacer member so that the second longitudinal axis is closer to the first end of the first member than to the second end, the second spacer member extending beyond opposing sides of the first spacer member.

9. An implant adapted to be inserted into a spine comprising:
   a. a first end plate having a first outer surface adapted to be substantially in contact with an upper vertebral body, and having a first inner surface having a first outer perimeter, the first inner surface having a first recessed arcuate channel formed therein, the first recessed arcuate channel having ends spaced inwardly from the first outer perimeter;
   b. a second end plate having a second outer surface adapted to be substantially in contact with a lower vertebral body, and having a second inner surface having a second outer perimeter, the second inner surface having a second recessed arcuate channel formed therein, the second recessed arcuate channel having ends spaced inwardly from the second outer perimeter;

c. a first keel protruding from the first outer surface and extending lengthwise between a first lateral end and a second lateral end of the first end plate;

d. a second keel protruding from the second outer surface and oriented to be substantially parallel to the first keel; and e. a crossbar spacer disposed between the first end plate and the second end plate, the crossbar spacer including i. a first spacer beam in the first arcuate channel having a curved outer side surface centered about a first longitudinal axis and having a first end and a second end; and ii. a second spacer beam perpendicular to the first spacer beam in the second arcuate channel having a curved outer side surface centered about a second longitudinal axis, the first spacer beam being disposed relative to the second spacer beam so that the second longitudinal axis is closer to the first end of the first beam than to the second end, the first and second spacer beams each respectively extending beyond opposing sides of each other.

10. An implant adapted to be inserted between adjacent vertebral bodies in a spine, the implant comprising:

a. an articulating unit having an outer surface adapted to be substantially in contact with a vertebral body, the articulating unit have first and second opposing inner surfaces, the first inner surface having a first outer perimeter and having a first recessed arcuate channel formed therein, the first recessed arcuate channel having ends spaced inwardly from the first outer perimeter, the second inner surface having an outer perimeter, and having a second recessed arcuate channel formed therein, the second recessed arcuate channel having ends spaced inwardly from the second outer perimeter;

b. a crossbar spacer positioned within the channels of the articulating unit, wherein the crossbar spacer allows at least a portion of the articulating unit to rotate in association with flexion and extension of at least one of the vertebral bodies, wherein the crossbar spacer includes i. a first spacer beam having a curved outer side surface centered about a first longitudinal axis, and having a first end and a second end; and ii. a second spacer beam perpendicular to the first spacer beam having a curved outer side surface centered about a second longitudinal axis, the first spacer beam being disposed relative to the second spacer beam so that the second longitudinal axis is closer to the first end of the first beam than to the second end, the first and second spacer beams each respectively extending beyond opposing sides of each other; and c. a keel extending from the outer surface of the articulating unit and oriented to extend lengthwise between a first lateral end and a second lateral end of the articulating unit.

11. An implant adapted to be inserted between adjacent vertebral bodies in a spine, the implant comprising:

a. an articulating unit having an outer surface adapted to be substantially in contact with a vertebral body, the articulating unit have first and second opposing inner surfaces, the first inner surface having a first outer perimeter and having a first recessed arcuate channel formed therein, the first recessed arcuate channel having ends spaced inwardly from the first outer perimeter, the second inner surface having an outer penmeter, and having a second recessed arcuate channel formed therein, the second recessed arcuate channel having ends spaced inwardly from the second outer perimeter, the channels of the articulating unit having a crossbar spacer therein, wherein the crossbar spacer includes i. a first spacer beam having a curved outer side surface centered about a first longitudinal axis, and having a first end and a second end; and ii. a second spacer beam perpendicular to the first spacer beam having a curved outer side surface centered about a second longitudinal axis, the first spacer beam being disposed relative to the second spacer beam so that the second longitudinal axis is closer to the first end of the first beam than to the second end, the first and second spacer beams each respectively extending beyond opposing sides of each other; and b. a keel extending from the outer surface of the articulating unit and oriented to extend lengthwise between a first lateral end and a second lateral end of the unit.

12. An interspinous disk replacement implant, comprising:

an articulating unit having an outer surface adapted to be substantially in contact with a vertebral body, and having inwardly facing inner surfaces, each having an arcuate channel formed therein, the arcuate channels each having ends spaced inwardly from the first outer perimeter;

a crossbar spacer positioned within the channels of the articulating unit, wherein the crossbar spacer includes a first spacer beam and a second spacer beam perpendicular to the first spacer beam, the first and second spacer beams being circular in cross-section, wherein the first spacer beam includes a first end and a second end and is disposed relative to the second spacer beam so that the second longitudinal axis is closer to the first end of the first beam than to the second end, the first and second spacer beams each respectively extending beyond opposing sides of each other; and at least one keel extending from the articulating unit.

13. In an interspinous disk replacement implant in a spine, the improvement comprising:

a. an articulating unit have first and second opposing inner surfaces, the first inner surface having a first outer perimeter and having a first recessed arcuate channel formed therein, the first recessed arcuate channel having ends spaced inwardly from the first outer perimeter, the second inner surface having an outer perimeter, and having a second recessed arcuate channel formed therein, the second recessed arcuate channel having ends spaced inwardly from the second outer perimeter;

b. a crossbar spacer in contact with an inner surface the implant, wherein the crossbar spacer accommodates flexion and extension movement of the spine, wherein the crossbar spacer includes i. a first spacer beam having a curved outer side surface centered about a first longitudinal axis, and having a first end and a second end; and ii. a second spacer beam perpendicular to the first spacer beam having a curved outer side surface centered about a second longitudinal axis, the first spacer beam being disposed relative to the second spacer beam so that the second longitudinal axis is closer to the first end of the first beam than to the second end, the first and second spacer beams each respectively extending beyond opposing sides of each other; and c. a keel extending from an outer surface of the implant and adapted to be secured into a vertebral body, wherein the keel is approximately perpendicular to the sagittal plane of the spine.

14. An interspinous disk replacement implant, comprising:
an articulating unit having an outer surface adapted to be substantially in contact with a vertebral body, and having inwardly facing inner surfaces, each having an arcuate channel formed therein, the arcuate channels each having ends spaced inwardly from the first outer perimeter;
a crossbar spacer positioned within the arcuate channels of the articulating unit, wherein the crossbar spacer includes a first spacer beam and a second spacer beam perpendicular to the first spacer beam, the first and second spacer beams being circular in cross-section,
wherein the first spacer beam includes a first end and a second end and is disposed relative to the second spacer beam so that the second longitudinal axis is closer to the first end of the first beam than to the second end, the first and second spacer beams each respectively extending beyond opposing sides of each other; and
at least one keel extending from an outer surface of the implant from a first side to a second side, the at least one keel adapted to be insertable into the spine.

15. An intervertebral implant adapted to be inserted between adjacent vertebral bodies comprising:
a. a first end plate adapted to mate with a first vertebral body, the first end plate further comprising:
i. a first inner surface having a first outer perimeter, the first inner surface having a first recessed arcuate channel formed therein, the first recessed arcuate channel having ends spaced inwardly from the first outer perimeter;
ii. a first outer surface; and
iii. a first keel on the first outer surface, wherein the first keel is oriented substantially perpendicular to the sagittal plane of the vertebral bodies;
b. a second end plate having a second outer surface adapted to mate with a second vertebral body, the second end plate including a second inner surface opposed to the first inner surface and having a second outer perimeter, the second inner surface having a second recessed arcuate channel formed therein, the second recessed arcuate channel having ends spaced inwardly from the second outer perimeter; and
c. a crossbar spacer positioned between the first and second inner surfaces in the arcuate channels, wherein the crossbar spacer includes
i. a first spacer beam having a curved outer side surface centered about a first longitudinal axis and having a first end and a second end; and
ii. a second spacer beam perpendicular to the first spacer beam having a curved outer side surface centered about a second longitudinal axis, the first spacer beam being disposed relative to the second spacer beam so that the second longitudinal axis is closer to the first end of the first beam than to the second end, the first and second spacer beams each respectively extending beyond opposing sides of each other.

16. The implant of claim 15 wherein the first keel further comprises a plurality of angled teeth.

17. The implant of claim 15 wherein the second end plate further comprises a second keel on the second outer surface, wherein the second keel is substantially perpendicular to the sagittal plane of the vertebral bodies.

18. The implant of claim 17 wherein the second keel further comprises a plurality of angled teeth.

19. The implant of claim 15 wherein the first keel further comprises a plurality of keels on the first outer surface.

20. The implant of claim 15 wherein the first spacer beam is in contact with the first inner surface; and
the second spacer beam is in contact with the second inner surface.

21. The implant of claim 15 wherein the first channel is oriented in a direction extending between an anterior end and a posterior end of the first end plate.

22. The implant of claim 15 wherein the first channel is oriented in a direction between a first lateral end and a second lateral end of the first end plate.

23. The implant of claim 15 wherein the second channel is oriented in a direction extending between an anterior end and a posterior end of the second end plate.

24. The implant of claim 15 wherein the second channel is oriented in a direction between a first lateral end and a second lateral end of the second end plate.

25. An implant adapted to be inserted between adjacent vertebral bodies, comprising:
a. a first end plate having a first outer surface adapted to mate with a first vertebral body, the first end plate further comprising:
i. a first inner surface having a first outer perimeter, the first inner surface having a first recessed arcuate channel formed therein, the first recessed arcuate channel having ends spaced inwardly from the first outer perimeter; and
ii. a first keel on the first outer surface, wherein the first keel is oriented substantially perpendicular to the sagittal plane of the vertebral bodies;
b. a second end plate having a second outer surface adapted to mate with a second vertebral body, the second end plate further comprising:
i. a second inner surface opposed to the first inner surface, the second inner surface having a second outer perimeter, the second inner surface having a second recessed arcuate channel formed therein, the second recessed arcuate channel having ends spaced inwardly from the second outer perimeter; and
ii. a second keel on the second outer surface, wherein the second keel is oriented substantially perpendicular to the sagittal plane of the vertebral bodies; and
c. a crossbar spacer in contact with the first and second inner surfaces, wherein the crossbar spacer includes
i. a first spacer beam having a curved outer side surface centered about a first longitudinal axis and having a first end and a second end; and
ii. a second spacer beam perpendicular to the first spacer beam having a curved outer side surface centered about a second longitudinal axis, the first spacer beam being disposed relative to the second spacer beam so that the second longitudinal axis is closer to the first end of the first beam than to the second end, the first and second spacer beams each respectively extending beyond opposing sides of each other.

26. The implant of claim 25 wherein the first keel further comprises a plurality of first keels on the first outer surface.

27. The implant of claim 25 wherein the first keel further comprises a plurality of teeth.

28. The implant of claim 25 wherein the second keel further comprises a plurality of second keels on the second outer surface.

29. The implant of claim 25 wherein the second keel further comprises a plurality of teeth.

30. The implant of claim 25 wherein the first spacer beam is in contact with the first inner surface; and
the second spacer beam is in contact with the second inner surface.

31. The implant of claim 25 wherein the first channel is oriented in a direction extending between an anterior end and a posterior end of the first end plate.

32. The implant of claim 25 wherein the first channel is oriented in a direction extending between a first lateral end and a second lateral end of the first end plate.

33. The implant of claim 25 wherein the second channel is oriented in a direction extending between an anterior end and a posterior end of the second end plate.

34. The implant of claim 25 wherein the second channel is oriented in a direction between a first lateral end and a second lateral end of the second end plate.

35. An intervertebral implant adapted to be inserted between adjacent vertebral bodies comprising:
 a. an articulating unit further comprising:
  i. an anterior end;
  ii. a posterior end;
  iii. a first lateral end;
  iv. a second lateral end;
  v. a first inner surface having a first outer perimeter, the first inner surface having a first recessed arcuate channel formed therein, the first recessed arcuate channel having ends spaced inwardly from the first outer perimeter; and
  vi. a second outer perimeter, the second inner surface having a second recessed arcuate channel formed therein, the second recessed arcuate channel having ends spaced inwardly from the second outer perimeter;
 b. a keel extending from the articulating unit and oriented in a lengthwise direction between the first and second lateral ends; and
 c. a crossbar spacer positioned within the first and second channels of the articulating unit, wherein the crossbar spacer includes
  i. a first spacer beam having a curved outer side surface centered about a first longitudinal axis, and having a first end and a second end; and
  ii. a second spacer beam perpendicular to the first spacer beam having a curved outer side surface centered about a second longitudinal axis, the first spacer beam being disposed relative to the second spacer beam so that the second longitudinal axis is closer to the first end of the first beam than to the second end, the first and second spacer beams each respectively extending beyond opposing sides of each other.

36. The implant of claim 35 wherein the keel further comprises at least one first keel extending from a first outer surface of the articulating unit.

37. The implant of claim 36 wherein the keel further comprises at least one second keel extending from a second outer surface of the articulating unit.

38. The implant of claim 35 wherein the first spacer beam is in contact with a first inner surface of the articulating unit; and
 the second spacer beam is in contact with a second opposed inner surface of the articulating unit.

39. The implant of claim 35 wherein the first channel is oriented lengthwise between the first and second lateral ends.

40. The implant of claim 35 wherein the first channel is oriented lengthwise between the anterior and posterior ends.

41. The implant of claim 35 wherein the second channel is oriented lengthwise between the first and second lateral ends.

42. The implant of claim 35 wherein the second channel is oriented lengthwise between the anterior and posterior ends.

* * * * *